(12) United States Patent
Tang et al.

(10) Patent No.: US 9,315,465 B2
(45) Date of Patent: Apr. 19, 2016

(54) PHOTOSTABLE AIE LUMINOGENS FOR SPECIFIC MITOCHONDRIAL IMAGING AND ITS METHOD OF MANUFACTURING THEREOF

(71) Applicant: THE HONG KONG UNIVERSITY OF SCIENCE AND TECHNOLOGY, Kowloon, Hong Kong (CN)

(72) Inventors: Benzhong Tang, Hong Kong (CN); Yuning Hong, Hong Kong (CN); Sijie Chen, Hong Kong (CN); Wai Tung Leung, Hong Kong (CN); Engui Zhao, Hong Kong (CN); Haiqin Deng, Hong Kong (CN)

(73) Assignee: THE HONG KONG UNIVERSITY OF SCIENCE AND TECHNOLOGY, Hong Kong (CN)

( * ) Notice: Subject to any disclaimer, the term of this patent is extended or adjusted under 35 U.S.C. 154(b) by 8 days.

(21) Appl. No.: 14/164,591

(22) Filed: Jan. 27, 2014

(65) Prior Publication Data
US 2014/0212359 A1    Jul. 31, 2014

Related U.S. Application Data

(60) Provisional application No. 61/849,536, filed on Jan. 29, 2013.

(51) Int. Cl.
*G01N 33/52*    (2006.01)
*C07D 217/04*   (2006.01)
*C07F 9/54*     (2006.01)
*C07D 209/08*   (2006.01)
*A61K 49/00*    (2006.01)

(52) U.S. Cl.
CPC .......... *C07D 217/04* (2013.01); *A61K 49/0023* (2013.01); *C07D 209/08* (2013.01); *C07F 9/5449* (2013.01); *G01N 33/52* (2013.01)

(58) Field of Classification Search
CPC ..... G01N 33/52; G01N 33/582; G01N 21/64; C07D 209/08; C07D 217/04; C07D 401/14
See application file for complete search history.

(56) References Cited

PUBLICATIONS

Synthesis, solvatochromism, aggregation-induced emission and cell imaging of tetraphenylaethene-containing BODPIY derivatives with large Stokes shifts, Chem. Commun., 2012, 48, 10099-10101.*

* cited by examiner

*Primary Examiner* — Michael G Hartley
*Assistant Examiner* — Jagadishwar Samala
(74) *Attorney, Agent, or Firm* — Nath, Goldberg & Meyer; Joshua B. Goldberg

(57) ABSTRACT

AIE (aggregation-induced emission)-active TPE derivatives, TPE-TPP, TPE-MitoR and TPE-IQ are contemplated. These specific TPE derivatives are useful as fluorescent agents for mitochondrial imaging and as apoptosis inducers. Possessing high specificity to mitochondria, superior photostability and appreciable tolerance to microenvironment change, TPE derivatives are well-suited imaging agents for mitochondrial targeting and morphological change tracking. Because of their synthetic flexibility, TPE derivatives can be further modified as dual-functional probes for an array of applications such as sensing of ROS, metal ions, or pH change in mitochondria.

7 Claims, 15 Drawing Sheets

US 9,315,465 B2

PHOTOSTABLE AIE LUMINOGENS FOR SPECIFIC MITOCHONDRIAL IMAGING AND ITS METHOD OF MANUFACTURING THEREOF

RELATED APPLICATIONS

The present patent application claims priority to provisional patent application No. 61/849,536, filed Jan. 29, 2013, which is incorporated by reference herein in its entirety.

TECHNICAL FIELD

The present subject matter relates to luminogens or salts thereof exhibiting aggregation-induced emission (AIE) that can image mitochondria with high selectivity and photo stability.

BACKGROUND

Mitochondria, the organelle found in almost all eukaryotic cells, play a vital role in the life and death of cells. Each mitochondria is composed of two concentric membranes, the inner membrane forming a series of folds that partially divide the interior matrix into communicating compartments. Mitochondria are generally ovoid or elongated in configuration; and uniquely contain their own genomic DNA, conventionally termed "mrDNA", which is circular in its three dimensional structure and constitutes a type that is chemically separate and distinct from the chromosomal DNA in the cell's nucleus.

The most prominent function of mitochondria is to produce ATP, the energy currency of the cell. The production of ATP involves a series of electron transport systems in the oxidation phosphorylation pathway, which is also found to be associated with the generation of reactive oxygen species (ROS). The production of ROS in mitochondria leads to the propagation of free radicals, damaging cells, and contributing to cell death, which is known as mitochondria-mediated apoptosis.

The morphology of mitochondria, though variable based upon cell type, cell-cycle stage, and intracellular metabolic state, is affected by and thus reflects cell functioning. The morphology is controlled by a set of proteins, mutations of which will cause several human diseases including degenerative diseases such as Parkinson's and Alzheimer's diseases. Recent reports also show that proteins participating in apoptosis can affect the morphology of mitochondria. Tracking the mitochondrial morphological change may give insight for studying apoptosis and degenerative conditions. The need to visualize and monitor mitochondria inside the cell is known.

The importance of monitoring the morphology, functionality, activity, and number of the mitochondria is associated with the possibility of proving the harmful effects of various substances and of showing mutations in the mitochondrial DNA. In the first case, for example, some anaesthetics have proved to be modifiers of mitochondrial activity (*Biochem. J.* 1990, 271, 269), while in the second case it has been proved that mutations of the mitochondrial DNA are often implicated in a number of neurodegenerative diseases such as Parkinson's and Alzheimer's and involve cell death by apoptosis or necrosis.

Fluorescent probes used to detect important biological events in living cells or animals have been in increasing demand in the biological and biomedical fields over the past two decades. Many kinds of fluorescent bioprobes have been developed, such as organic dyes, inorganic nanoparticles, and fluorescent polymers.

In this regard, fluorescent probes that can selectively illuminate cellular mitochondria are powerful tools for monitoring the morphological changes and studying these processes. To successfully observe the dynamic changes in a certain period of time, the probe must be photostable under the continual irradiation of light from fluorescent microscopes. Conventional fluorescent dyes for mitochondria staining have been developed. Their photostability, however, leaves much to be desired. Very diluted solutions of these dyes are used in the imaging process and such small numbers of the dye molecules can be quickly photobleached when a harsh laser beam is used as the excitation light source. The photostability cannot be improved by using higher fluorophore concentration due to the accompanying concentration-quenching effect.

Mitochondria targeting probes with different functions have been reported in the prior art, examples of which have been reported by Abbotto Alessandro (WO 2007/113321 A1), Zarling David A. (WO 2008/109740 A2), Dario C. Altieri (US 2009/0099080 A1), and Shibnath Ghosal (US 2008/0031862 A1). Generally, these previous disclosures face several problems, for example losing the specificity to mitochondria once the mitochondrial membrane potential is collapsed, suffering from aggregation-caused quenching, or even only having a complicated synthetic route. Accordingly, there remains a need in the art to address these issues.

SUMMARY

The present subject matter relates generally to AIE (aggregation-induced emission)-active TPE derivatives, TPE-TPP, TPE-MitoR and TPE-IQ. These specific TPE derivatives are useful as fluorescent agents for mitochondrial imaging and as apoptosis inducers. Possessing high specificity to mitochondria, superior photostability and appreciable tolerance to microenvironment change, TPE derivatives are well-suited imaging agents for mitochondrial targeting and morphological change tracking. Because of their synthetic flexibility, TPE derivatives can be further modified as dual-functional probes for an array of applications such as sensing of ROS, metal ions, or pH change in mitochondria.

In this regard, the present subject matter generally relates to triphenylphosphonium-functionalized, benzothiazolium-functionalized, or isoquinoline-functionalized AIE luminogens. These functional groups possess a positively charged moiety which facilitates the specificity of those AIE luminogens towards mitochondria. With the help of the hydrophobic AIE-active core, these luminogens are expected to have high tolerance to the changing microenvironment. Accordingly, any other functionalized group possessing a similarly charged moiety might be similarly useful herein.

Specifically, the present subject matter is directed to luminogens having aggregation-induced emission properties comprising a triphenylphosphonium-functionalized, benzothiazolium-functionalized, or isoquinoline-functionalized TPE derivative, wherein the TPE derivative comprises a backbone structure of a formula selected from the group consisting of:

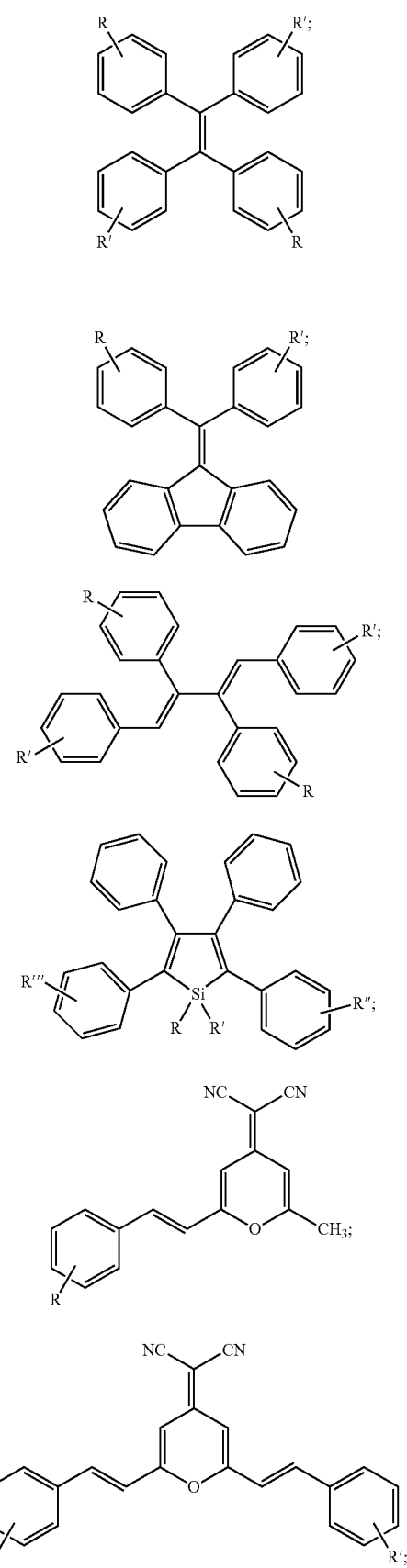
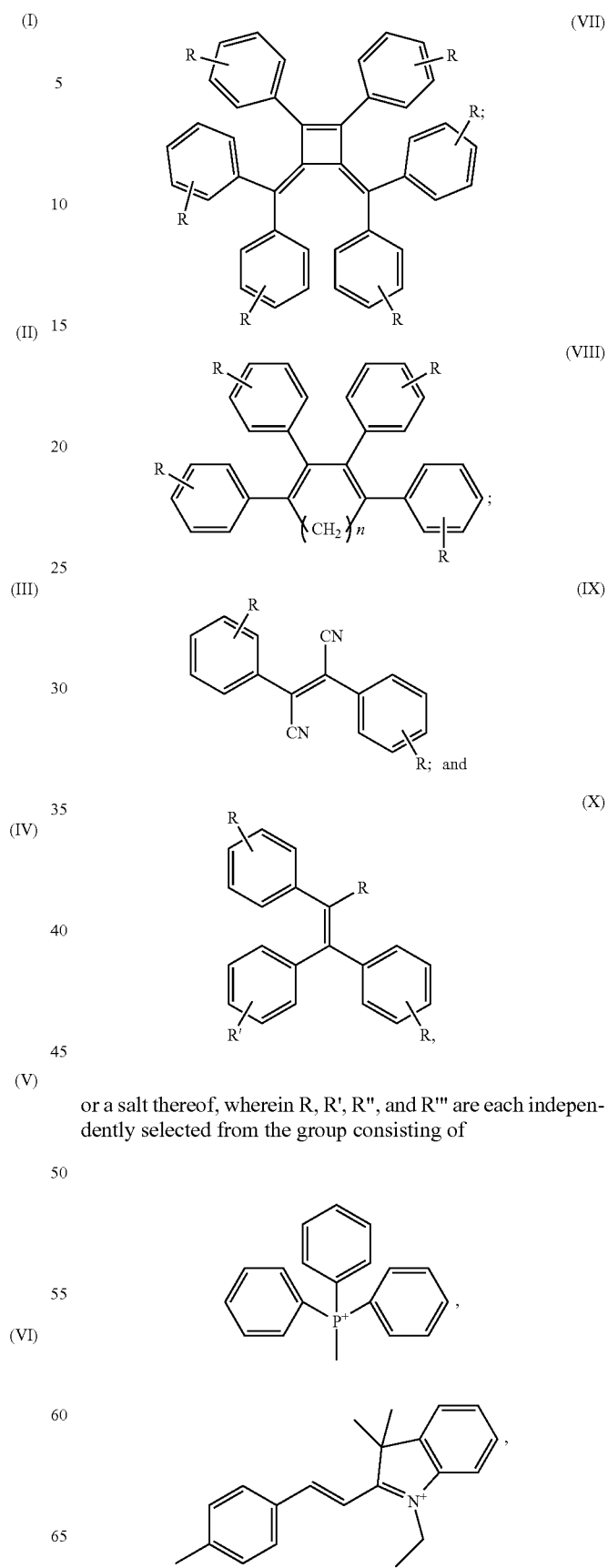
or a salt thereof, wherein R, R', R", and R'" are each independently selected from the group consisting of -continued

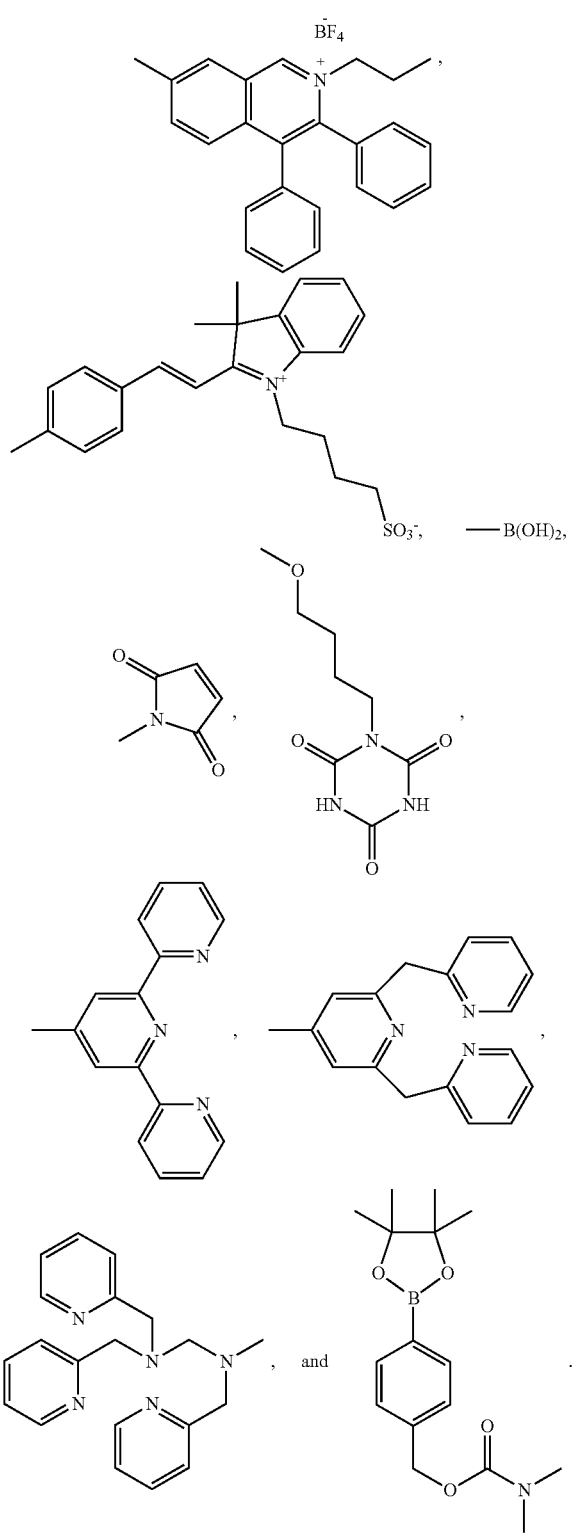

In addition, the present subject matter relates to a method of imaging mitochondria in cells comprising contacting one or more live cells with a luminogen as described herein, and imaging any mitochondrial activities.

Further, the present subject matter relates to a method for in vivo monitoring of cell apoptosis comprising injecting a subject with a luminogen as described herein and detecting fluorescence, wherein the triphenylphosphonium-functionalized, benzothiazolium-functionalized, or isoquinoline-functionalized TPE Derivative is used as an apoptosis inducer.

BRIEF DESCRIPTION OF THE DRAWINGS

Various embodiments will be described in detail with reference to the accompanying drawings.

FIG. 17C shows panels A and B merged.

FIG. 18C shows panels A and B merged. FIG. 18D shows a bright field image of the imaging area. Excitation wavelength: 330-385 nm (for TPE-IQ) and 540-580 nm (for MT).

DETAILED DESCRIPTION

Definitions

Figure 1:
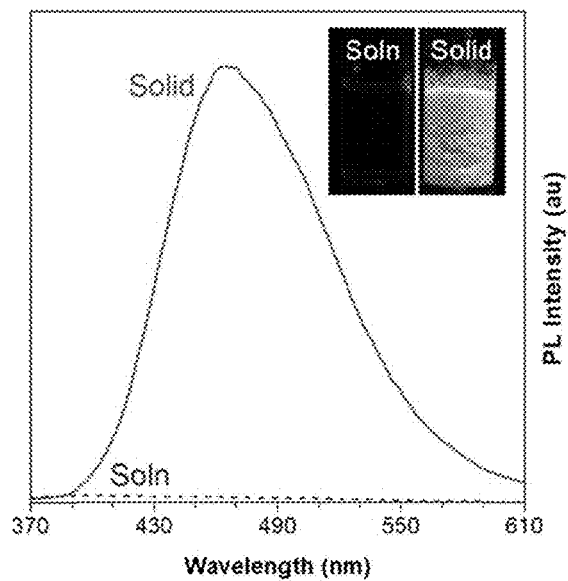
FIG. 1 shows the PL spectra of TPE-TPP in the solid and solution (soln) states. Inset: Photographs of DMF solution (left) and solid powder (right) of TPE-TPP taken under UV irradiation. Concentration of TPE-TPP: 10 μM; excitation wavelength: 321 nm.

All technical and scientific terms used herein have the same meanings as commonly understood by someone ordinarily skilled in the art to which the present subject matter belongs. The following definitions are provided for clarity.

The term "$\lambda_{ex}$" as used herein refers to excitation wavelength.

The phrase "aggregation-induced emission" or "AIE" as used herein refers to the phenomenon manifested by compounds exhibiting significant enhancement of light-emission upon aggregation in the amorphous or crystalline (solid) states whereas they exhibit weak or almost no emission in dilute solutions.

The term "alkyl" as used herein refers to a branched or unbranched hydrocarbon chain comprising a designated number of carbon atoms. For example, a $C_1$-$C_6$ straight or branched alkyl hydrocarbon chain contains 1 to 6 carbon atoms, and includes but is not limited to methyl, ethyl, propyl, iso-propyl, butyl, iso-butyl, tert-butyl, n-pentyl, n-hexyl, and the like. In one embodiment, the "alkyl" chain may be unsubstituted or is substituted by one or more substituents. It is also contemplated as with the scope of the present subject matter that "alkyl" may also refer to a hydrocarbon chain wherein any of the carbon atoms of the alkyl are optionally replaced with O, NH, S, or $SO_2$. For example, carbon 2 of n-pentyl can be replaced with O to form propyloxymethyl.

The term "alkoxy group" refers to an alkyl group singularly bonded to an oxygen atom. The range of alkoxy groups is great, the simplest being methoxy ($CH_3O$—).

The term "aryl" refers to an aromatic carbocyclic group having a single ring, for example a phenyl ring; multiple rings, for example biphenyl; or multiple condensed rings in which at least one ring is aromatic, for example naphthyl, 1,2,3,4-tetrahydronaphthyl, anthryl, or phenanthryl, which can be unsubstituted or substituted with one or more other substituents.

The term "biomacromolecule" as used herein refers to a very large molecule, such as a protein, nucleic acid, or polysaccharide of biological origin.

The term "cycloalkyl" as used herein refers to an organic cyclic substituent comprising a designated number of carbon atoms. For example, a $C_3$-$C_8$ cycloalkyl contains three to eight carbon atoms forming a three, four, five, six, seven, or eight-membered ring, including, for example, a cyclopropyl, cyclobutyl, cyclopentyl, cyclohexyl, cycloheptyl, or cyclooctyl ring, and the like. In one embodiment, the "cycloalkyl" may be unsubstituted or is substituted by one or more substituents.

The term "DMF" as used herein refers to dimethylformamide, which is an organic compound with the formula $(CH_3)_2NC(O)H$. It is a common solvent for chemical reactions.

The phrase "emission intensity" as used herein refers to the magnitude of fluorescence/phosphorescence normally obtained from a fluorescence spectrometer or a fluorescence microscopy measurement.

The term "fluorophore" as used herein refers to a fluorescent chemical compound that can re-emit light upon light excitation. Fluorophores typically contain several combined aromatic groups, or plane or cyclic molecules with several π bonds. Fluorophores can be used as tracers in fluids, dyes for staining certain structures, substrates of enzymes, or probes or indicators. Fluorophores absorb light energy of a specific wavelength and re-emit light at a longer wavelength. The absorbed wavelengths, energy transfer efficiency, and time before emission depend on both the fluorophore structure and its chemical environment, as the molecule in its excited state interacts with surrounding molecules.

The phrase "fluorescence resonance energy transfer" or "FRET" as used herein refers to a mechanism describing energy transfer between two chromophores. A donor chromophore, initially in its electronic excited state, may transfer energy to an acceptor chromophore through nonradiative dipole-dipole coupling. The efficiency of this energy transfer is inversely proportional to the sixth power of the distance between donor and acceptor making FRET extremely sensitive to small distances.

The term "heteroaryl" as used herein refers to a heterocycle in which at least one ring is aromatic. A heterocycle is a saturated, unsaturated, or aromatic carbocyclic group having a single ring, multiple rings, or multiple condensed rings, and having at least one hetero atom such as nitrogen, oxygen, or sulfur within at least one of the rings. A heteroaryl can also encompass a heteroalkyl or heterocycloakyl. In one embodiment, the "heteroaryl" may be unsubstituted or is substituted by one or more substituents.

The term "luminogen" as used herein refers to a chemical compound that manifests luminescence.

The term "nanoparticle" as used herein refers to any microscopic particle or particle population having a mean diameter of about 100 or less nanometers (nm); less than about 90 nm; less than about 80 nm; less than about 70 nm; less than about 60 nm; less than about 50 nm; or having a mean diameter of from 1 nm to less than 100 nm; from 10 nm to less than 100 nm; from 20 nm to less than 100 nm; from 30 nm to less than 100 nm; from 40 nm to less than 100 nm; from 50 nm to less than 100 nm; from 10 nm to 90 nm; from 20 nm to 80 nm; or having a mean diameter of from 30 nm to 70 nm. In an embodiment, greater than 99% of the nanoparticles of a nanoparticle population have a mean diameter falling within a described range; greater than about 90% of the microparticles have a mean diameter falling within a described range; greater than about 80% of the microparticles have a mean diameter falling within a described range; greater than about 70% of the microparticles have a mean diameter falling within a described range; greater than about 60% of the microparticles have a mean diameter falling within a described range; greater than about 50% of the microparticles have a mean diameter falling within a described range; greater than about 40% of the microparticles have a mean diameter falling within a described range; greater than about 30% of the microparticles have a mean diameter falling within a described range; greater than about 20% of the microparticles have a mean diameter falling within a described range; or greater than about 10% of the microparticles have a mean diameter falling within a described range.

The term "NHS" as used herein refers to N-hydroxysuccinimide, which is commonly used in organic chemistry or biochemistry as an activating reagent for carboxylic acids.

The term "TPE" as used herein refers to a tetraphenylethylene.

The phrase "unsaturated alkyl" as used herein refers to a branched or unbranched unsaturated hydrocarbon chain comprising a designated number of carbon atoms, and may also be referred to as an "alkenyl" or "alkynyl." For example, a $C_2$-$C_6$ straight or branched alkenyl hydrocarbon chain contains 2 to 6 carbon atoms having at least one double bond, and includes but is not limited to ethenyl, propenyl, iso-propenyl, butenyl, iso-butenyl, tert-butenyl, n-pentenyl, n-hexenyl, and the like. It is also contemplated as within the scope of the present subject matter that "unsaturated alkyl" may also refer to an unsaturated hydrocarbon chain wherein any of the carbon atoms of said unsaturated alkyl are optionally replaced with O, NH, S, or $SO_2$. For example, carbon 2 of 4-pentene can be replaced with O to form (2-propene)oxymethyl. In one embodiment, the "unsaturated alkyl" may be unsubstituted or is substituted by one or more substituents.

The term "a" or "an" as used herein includes the singular and the plural, unless specifically stated otherwise. Therefore, the term "a," "an," or "at least one" can be used interchangeably in this application.

Throughout the application, descriptions of various embodiments use the term "comprising;" however, it will be understood by one of skill in the art, that in some specific instances, an embodiment can alternatively be described using the language "consisting essentially of" or "consisting of."

For the purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The present subject matter is directed to luminogens having aggregation-induced emission properties comprising a triphenylphosphonium-functionalized, benzothiazolium-functionalized, or isoquinoline-functionalized TPE derivative, wherein the TPE derivative comprises a backbone structure of a formula selected from the group consisting of:

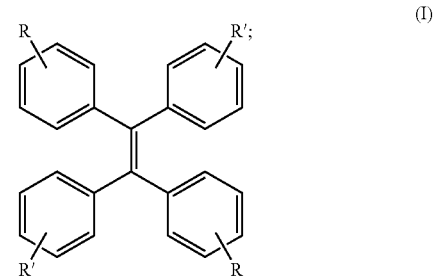

(I)

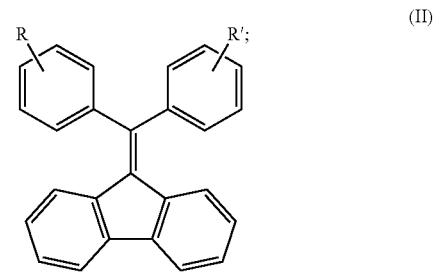

(II)

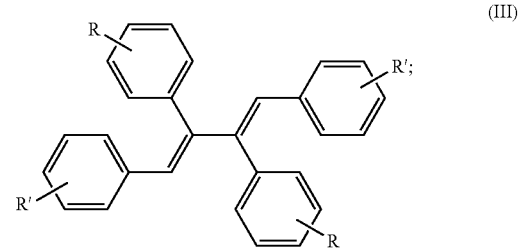

(III)

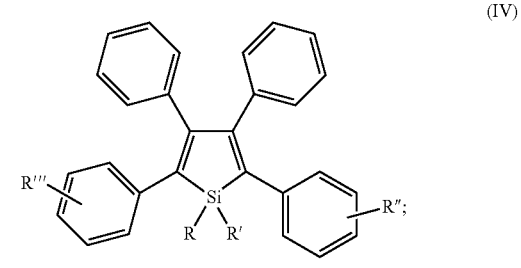

(IV)

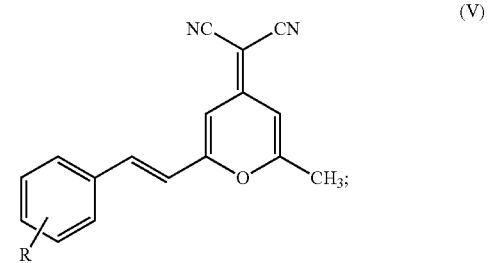

(V)

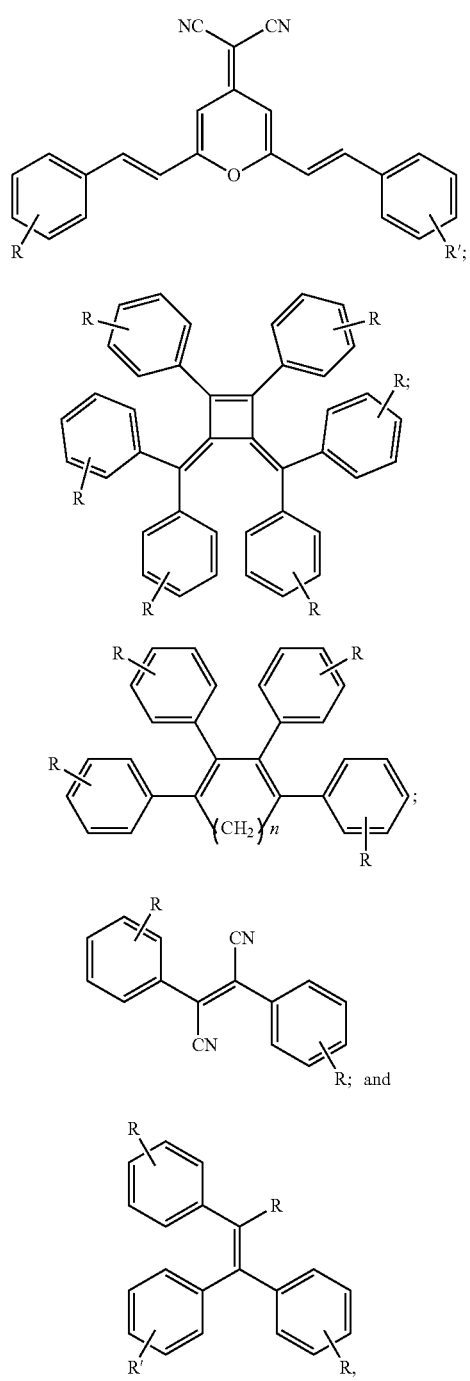
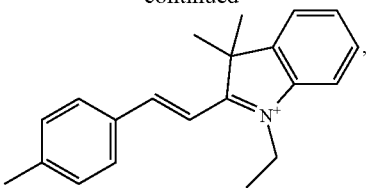
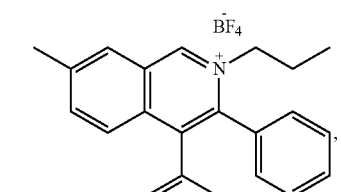
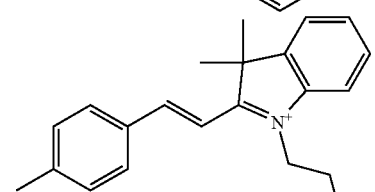
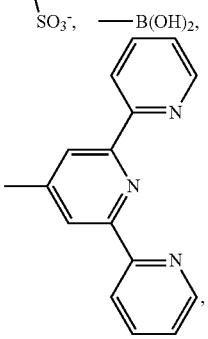
or a salt thereof, wherein R, R', R", and R'" are each independently selected from the group consisting of
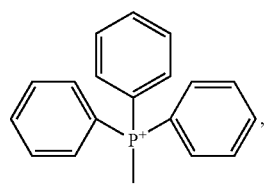

In one embodiment, the luminogen is TPE or a derivative thereof. In this regard, the TPE can have one or more groups selected from the group consisting of triphenylphosphonium, benzothiazolium, and isoquinoline groups.

The luminogens described herein are almost non-fluorescent when molecularly dissolved but become highly emissive in the aggregate state with fluorescence increasing along with the increase of luminogen (and thus, fluorophore) concentration. That is, the present luminogens exhibit an AIE effect. Restriction of intramolecular motions (RIM) is a likely main cause for this AIE effect.

In this regard, lipophilic AIE molecules form nanoaggregates in aqueous solution spontaneously because of their hydrophobic nature. The nanoaggregates of the present AIE molecules possess better photostability than single fluorescent molecule in dilute solutions.

In a particular embodiment, the present subject matter relates to a method of imaging mitochondria in cells comprising contacting one or more live cells with a luminogen described herein, and imaging any mitochondrial activities. To achieve the specificity to mitochondria, the present AIE luminogens are decorated with mitochondria targeting moieties. For example, tetraphenylethene (TPE), an archetypal AIE luminogen, was synthesized and functionalized with triphenylphosphonium (TPP) groups to produce TPE-TPP, the chemical structure of which is shown below:

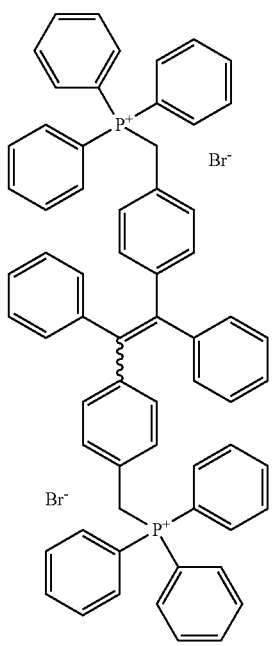

TPE-TPP

The TPP functional group facilitates the entrance of molecular probes into mitochondria by its lipophilicity and electrophoretic force. TPE-TPP was synthesized via a multistep reaction shown in the reaction scheme below.

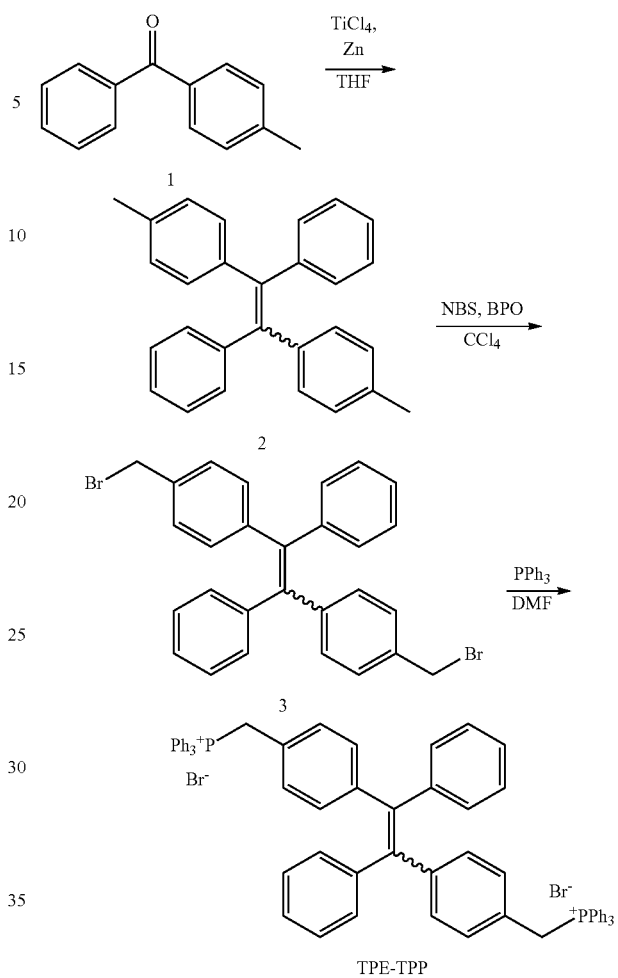

TPE-TPP

As shown below, TPE-TPP can light up mitochondria (i.e., the organelles where cellular respiration occurs) specifically in live cells with superior photostability that enables the observation of mitochondrial morphological changes. In this regard, the formation of nanoaggregates of TPE-TPP when dispersed in aqueous media may facilitate the dye to diffuse across the cell membrane to accumulate in the mitochondrial region. Due to the AIE feature, the nanoaggregates of TPE-TPP are much brighter emitters than its single molecular form because the condensed packing in the aggregate state constrains the intramolecular motions and blocks the nonradiative decay channels. When exposed to excitation light, the outermost layer of the nanoaggregates may be photobleached. However, the condensed particles can prevent further photobleaching and photo-oxidation by avoiding oxygen diffusion into the particles. For MitoTracker® Red FM, unfortunately, the working concentration is so low that even when accumulated in the mitochondrial matrix, it presents as individual molecule which will be destroyed with ease by the strong excitation light.

Mitochondria continuously oxidize substrates and maintain a proton gradient across the lipid bilayer with very large membrane potential ($\Delta\Psi_m$) of around −180 mV. This value is double of the plasma membrane of excitable cells and approximately six times larger than non-excitable cell plasma membrane. Due to this large membrane potential gradient, mitochondria drive cationic species such as TPP into the matrix. As a result, their accumulation in mitochondria is 100-500-fold higher than in other parts of the cell.

In another specific embodiment, TPE was synthesized and functionalized with MitoTracker® Red FM groups, having a chemical structure of:

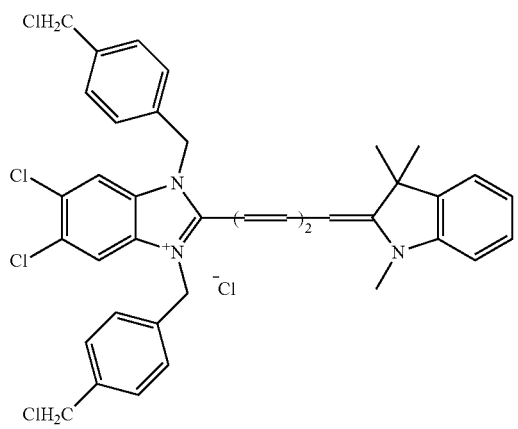

to produce TPE-MitoR, the chemical structure of which is shown below:

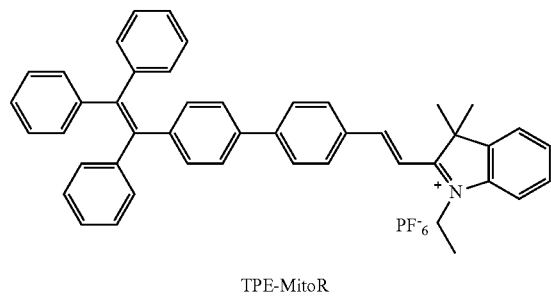

TPE-MitoR

TPE-MitoR was synthesized via an one-step reaction shown in the reaction scheme below.

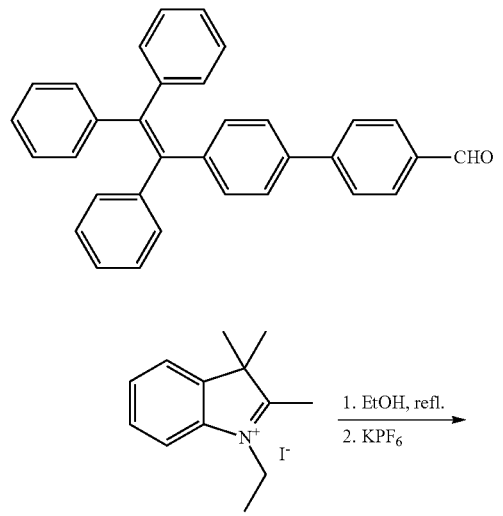

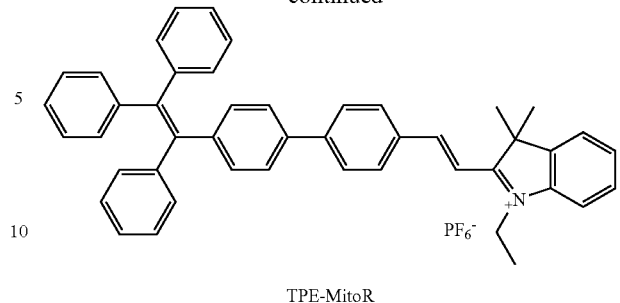

TPE-MitoR

In another specific embodiment, TPE was synthesized and reacted to produce TPE-IQ, the chemical structure of which is shown below:

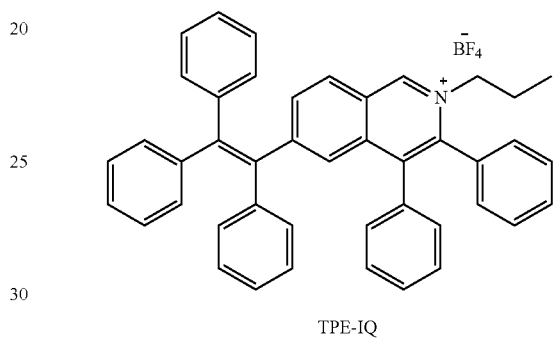

TPE-IQ

TPE-IQ was synthesized via an one-step reaction shown in the reaction scheme below.

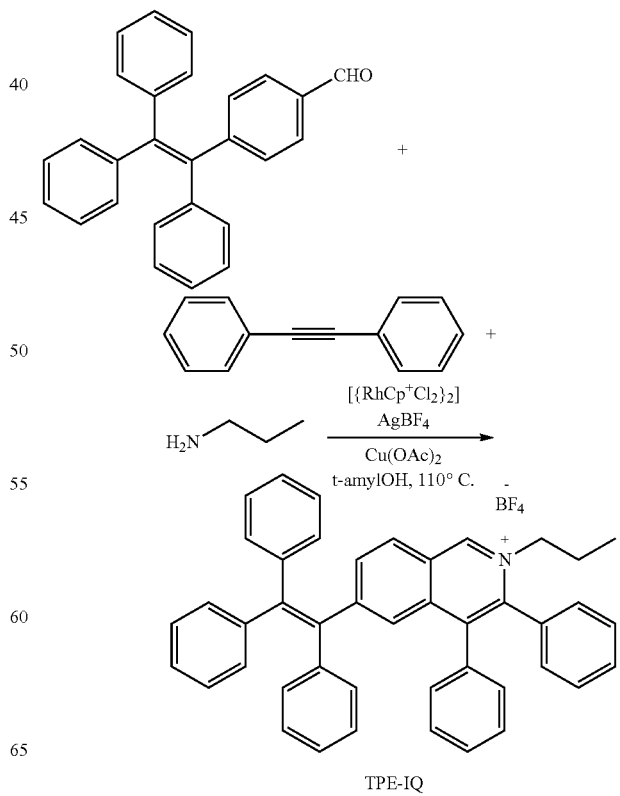

TPE-IQ

In a further embodiment, the present subject matter relates to in vitro and in vivo imaging of cell apoptosis using a bioprobe labeled with heterocycle-functionalized tetraphenylethene (TPE) derivatives.

EXAMPLES

Having described the subject matter, the following examples are given to illustrate various embodiments and specific applications of the present subject matter. These specific examples are not intended to limit the scope of the subject matter described in this application.

Example 1

Synthesis of TPE-TPP

Figure 2:
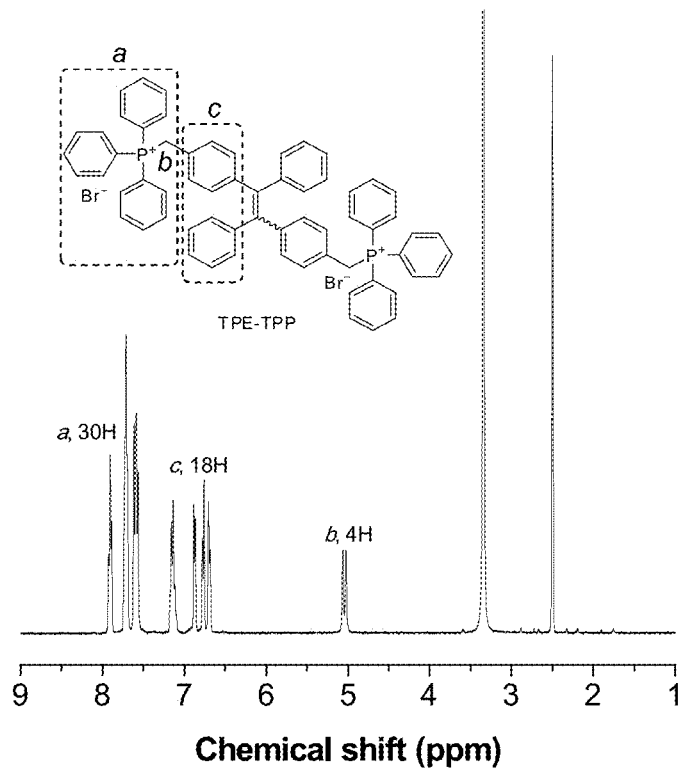
FIG. 2 shows $^1$H-NMR spectrum of TPE-TPP in DMSO-$d_6$.
Figure 3:
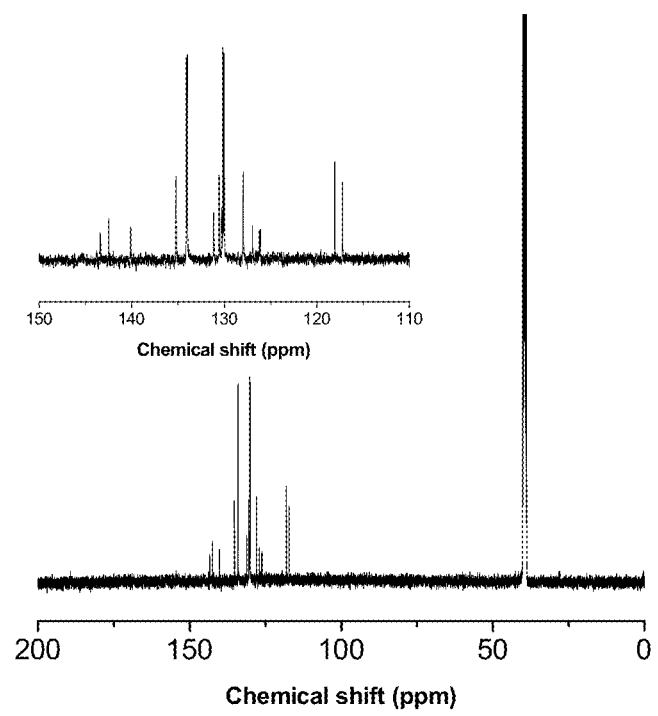
FIG. 3 shows $^{13}$C-NMR spectrum of TPE-TPP in DMSO-$d_6$.
Figure 4:
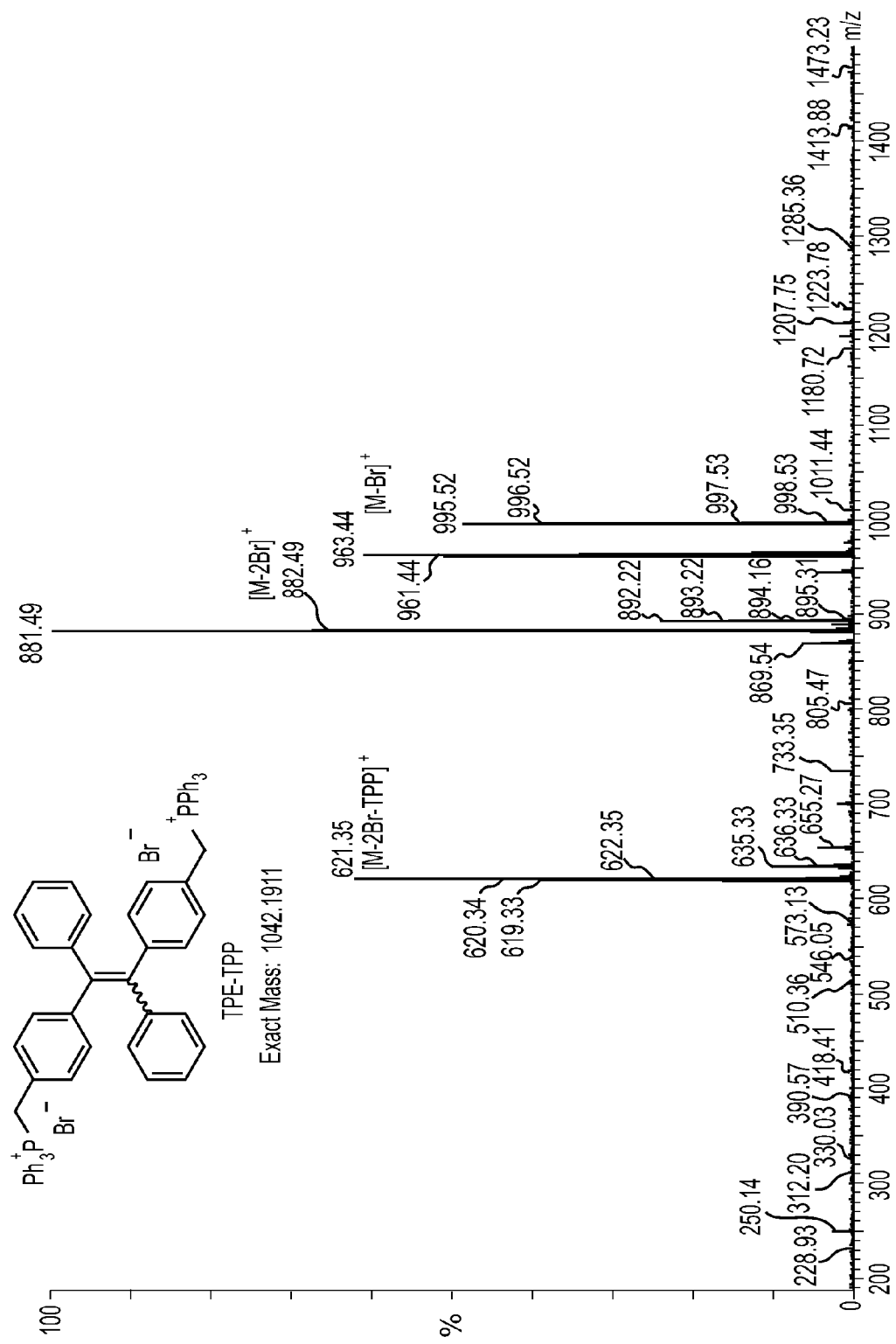
FIG. 4 shows mass spectrum (MALDI-TOF) of TPE-TPP.

The TPE core was synthesized simply from a McMurry coupling reaction. TPP was attached through bromination and subsequent reaction with triphenylphosphine. The product was characterized by NMR and mass spectroscopy and both of them gave satisfactory analysis data corresponding to their molecular structure (FIGS. 2-4). Although carrying positive charges, TPE-TPP has relatively poor solubility in aqueous solution but it is completely soluble in polar solvents such as DMF and DMSO.

Figure 5:
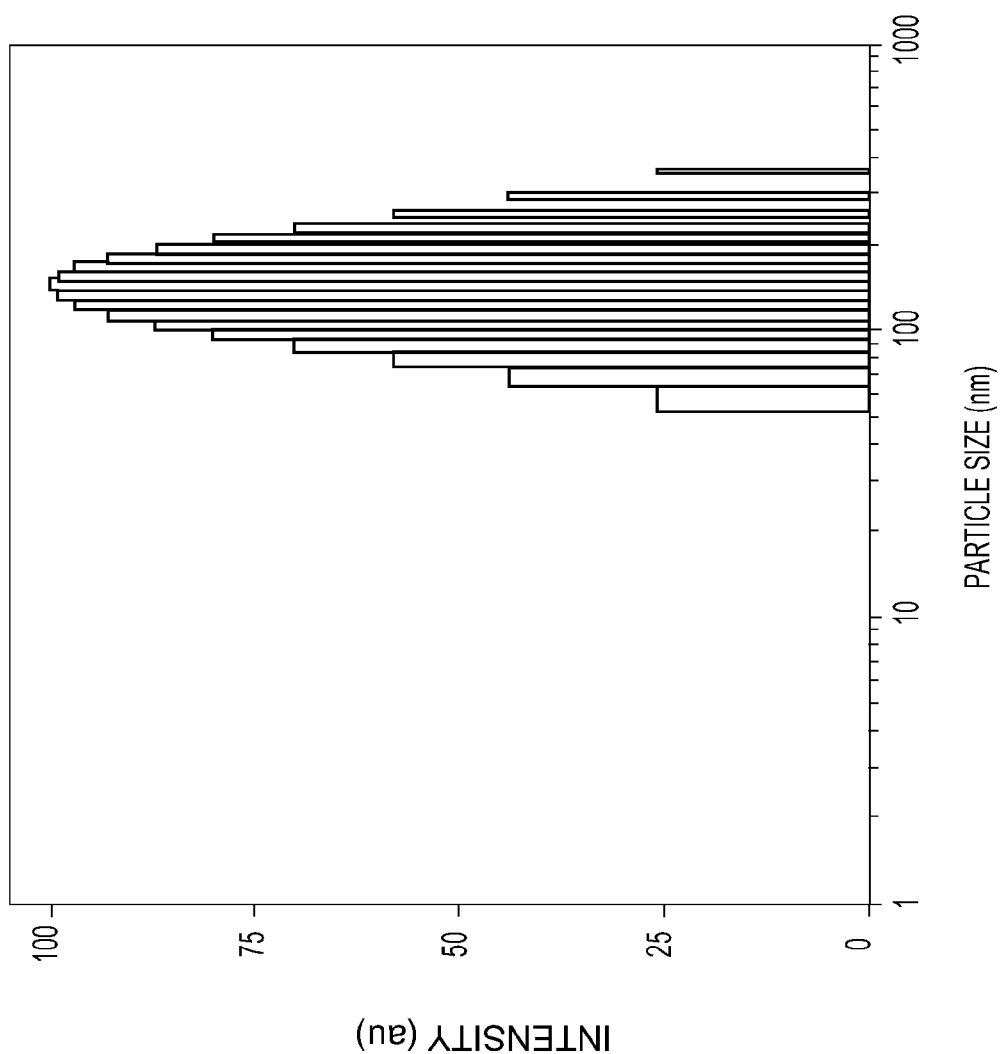
FIG. 5 shows a particle size analysis of TPE-TPP nanoaggregate in PBS.

TPE-TPP shows typical AIE features as shown in FIG. 1. The DMF solution of TPE-TPP was almost non-emissive while the solid state is strongly luminescent at 466 nm. Particle size analysis reveals the existence of particles with average size of 144 nm in aqueous solution containing 0.1% DMSO, the identical condition for cell staining, confirming that the TPE-TPP molecules have indeed formed aggregates in nano-scale (FIG. 5). The scheme of synthesis of said TPP-functionalized TPE is as follow:

Synthesis of 1,2-Bis(4-methylphenyl)-1,2-diphenylethene (2)

A suspension of 4-methylbenzophenone (1, 3.6 g, 10.0 mmol), TiCl$_4$ (1.9 g, 10.0 mmol), and Zn dust (1.3 g, 20.0 mmol) in dry THF (100 mL) was refluxed for 20 h. Afterward, the reaction mixture was cooled to room temperature and filtered. The filtrate was evaporated and the crude product was purified on a silica-gel column using DCM as eluent. Compound 2 was isolated as white solid in 94% yield. $^1$H NMR (300 MHz, CDCl$_3$), δ (TMS, ppm): 7.11-7.00 (m, 10H), 6.91 (d, 8H), 2.26 (d, 6H). $^{13}$C NMR (75 MHz, CDCl$_3$), δ (TMS, ppm): 144.8, 141.6, 141.1, 136.6, 132.0, 131.9, 129.0, 128.2, 126.9, 21.9. m/z (FAB) 360.2 [M$^+$]; calc. 360.2.

Synthesis of 1,2-Bis[4-(bromomethyl)phenyl]-1,2-diphenylethene (3)

To a mixture of 2 (1.8 g, 5.0 mmol) and NBS (1.7 g, 10.0 mmol) in CCl$_4$ was added catalytic amount of BPO at room temperature. The mixture was stirred and heated to reflux for 8 h. After filtration and solvent evaporation, the product was purified by silica gel chromatography using DCM/hexane (1:4 v/v) as eluent. Compound 3 was isolated as pale yellow solid in 43% yield. $^1$H NMR (300 MHz, CDCl$_3$), δ (TMS, ppm): 7.14-7.07 (m, 10H), 7.02-6.96 (m, 8H), 4.41 (d, 4H). $^{13}$C NMR (75 MHz, CDCl$_3$), δ (TMS, ppm): 144.4, 143.9, 141.5, 136.6, 132.3, 132.0, 129.2, 128.5, 127.4, 34.3. m/z (FAB) 518.0 [M$^+$]; calc. 518.2.

Synthesis of Bis(Triphenylphosphonium) Tetraphenylethene (TPE-TPP)

Triphenylphosphonium salt, TPE-TPP, was prepared from 3 (0.5 g, 1.0 mmol) and triphenylphosphine (1.0 g, 4.0 mmol) in DMF at 100° C. After stirring for 24 h, the solution was poured into large amount of toluene. The white precipitate was collected in 80% yield. $^1$H NMR (400 MHz, DMSO-d$_6$), δ (TMS, ppm): 7.90-7.55 (m, 30H), 7.16-6.66 (m, 18H), 5.039 (d, 4H). $^{13}$C NMR (100 MHz, DMSO-d$_6$), δ (TMS, ppm): 143.4, 142.5 140.1, 135.2, 134.0, 131.1, 130.6, 130.3, 130.1, 128.0, 127.0, 126.1, 118.1, 17.2, 40.21. m/z (MALDI-TOF) 882.49 [M−2Br)$^+$]; calc. 882.35. Anal. Calcd. C$_{64}$H$_{52}$Br$_2$P$_2$: C, 73.7; H, 5.0. Found: C, 73.7; H, 4.9.

Example 2

Synthesis of TPE-MitoR

A solution of 4-(1,2,2-Triphenylvinyl)benzaldehyde (436 mg, 1.00 mmol) and 3-Ethyl-2-methyl-1,3-benzothiazol-3-ium iodide (315 mg, 1.00 mmol) in dry EtOH (15 mL) was refluxed under nitrogen for 48 h. After cool to ambient temperature, the solvent was evaporated under reduced pressure. The solid was dissolved in acetone (5 mL) and a saturated aqueous solution of KPF$_6$ (5 mL) was then added. After stirring for 30 min, the solution was evaporated to dryness. The residue was purified by a silica gel column chromatography using dichloromethane and acetone mixture (5:1 v/v) as eluent to give a red product in 72% yield. HRMS (MALDI-TOF): m/z 751.2686 [M$^+$]; calcd 751.2803; 606.3170 [M$^+$-PF$_6^-$]; calcd 606.3155.

Example 3

Synthesis of TPE-IQ

A sealed tube containing [RhCp*Cl$_2$]$_2$ (2.0 mol %), AgBF$_4$ (0.30 mmol), Cu(OAc)$_2$ (0.30 mmol), aryl aldehyde (0.36 mmol) and internal alkyne (0.30 mmol) was evacuated and purged with nitrogen gas three times. Then, propylamine (0.45 mmol) and t-amyl alcohol (2.5 ml) were sequentially added to the system via syringe under a nitrogen atmosphere and the reaction mixture was allowed to stir at 110° C. for 3 h. When the reaction was complete, the mixture was cooled and diluted with CH$_2$Cl$_2$ (10 mL). The mixture was filtered through a Celite pad and the Celite pad was washed with CH$_2$Cl$_2$ (30 mL) and MeOH (20 mL). The combined filtrate was concentrated in vacuo and the residue was purified by alumina column chromatography using CH$_2$Cl$_2$/MeOH (100:1 v/v) as eluent to give pure product TPE-IQ as a greenish-yellow solid in 85% yield. $^1$H NMR (400 MHz, CDCl$_3$) δ 9.97 (s, 1H), 8.47 (d, J=8.5 Hz, 1H), 7.57 (d, J=8.7 Hz, 1H), 7.37-7.28 (m, 4H), 7.15 (m, 14H), 6.95 (d, J=6.7 Hz, 2H), 6.90 (t, J=7.3 Hz, 4H), 6.57 (d, J=7.3 Hz, 2H), 4.48 (t, J=7.6 Hz, 2H), 1.85 (m, 2H), 0.84 (t, J=7.3 Hz, 3H). $^{13}$C NMR (100 MHz, CDCl$_3$) δ 153.90, 149.95, 145.99, 143.82, 142.56, 141.95, 139.22, 138.83, 137.13, 134.60, 132.88, 131.58, 131.54, 131.38, 131.30, 130.97, 130.47, 130.28, 128.95, 128.79, 128.68, 128.52, 128.47, 127.96, 127.64, 127.57, 126.22, 60.89, 25.41, 10.91. HRMS (MALDI-TOF): m/z (cation) 578.2854 [M+, calcd 578.2842]; m/z (anion) 87.0018 [M$^+$, calcd 87.0035].

Example 4

Figure 6:
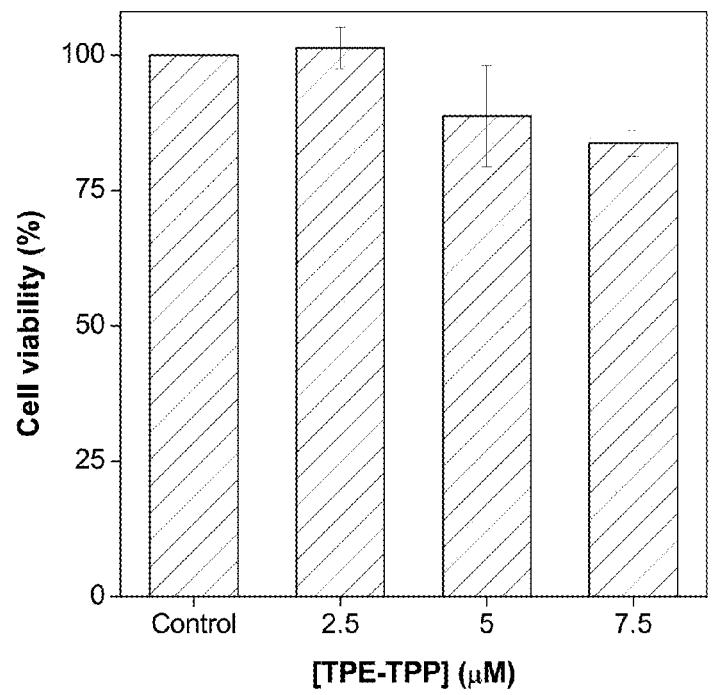
FIG. 6 shows the cytotoxicity of TPE-TPP on HeLa cells determined by the MTT assay.

Applying an organelle tracker into living sample, the cytotoxicity of the probe, TPE-TPP, was evaluated using the 3-(4, 5-dimethyl-2-thiazolyl)-2,5-diphenyltetrazolium bromide (MTT) assay (FIG. 6). The result shows that the cell viability is not significantly altered when up to 7.5 µM TPE-TPP is added to the culture medium.

TPE-TPP was then assessed for its ability to localize and stain mitochondria in living cells by fluorescence microscope. Cervical cancer HeLa cells were incubated with 5 µM TPE-TPP for 1 h and excess dyes were washed away by buffer solution. As shown in FIG. 7A, TPE-TPP stains specifically the mitochondrial region in HeLa cells. The reticulum structures of mitochondria were clearly visualized with the aid of the blue fluorescence of TPE-TPP.

Figure 7:
FIG. 7 shows fluorescent images of HeLa cells stained with (A) TPE-TPP (5 μM) for 1 h; (B) MitoTracker® Red FM (MT, 50 nM) for 15 min; and (C) Merged images of panels A and B. Excitation wavelength: 330-385 nm (for TPE-TPP) and 540-580 nm (for MT).
Figures 8A, 8B, 8C, 8D:
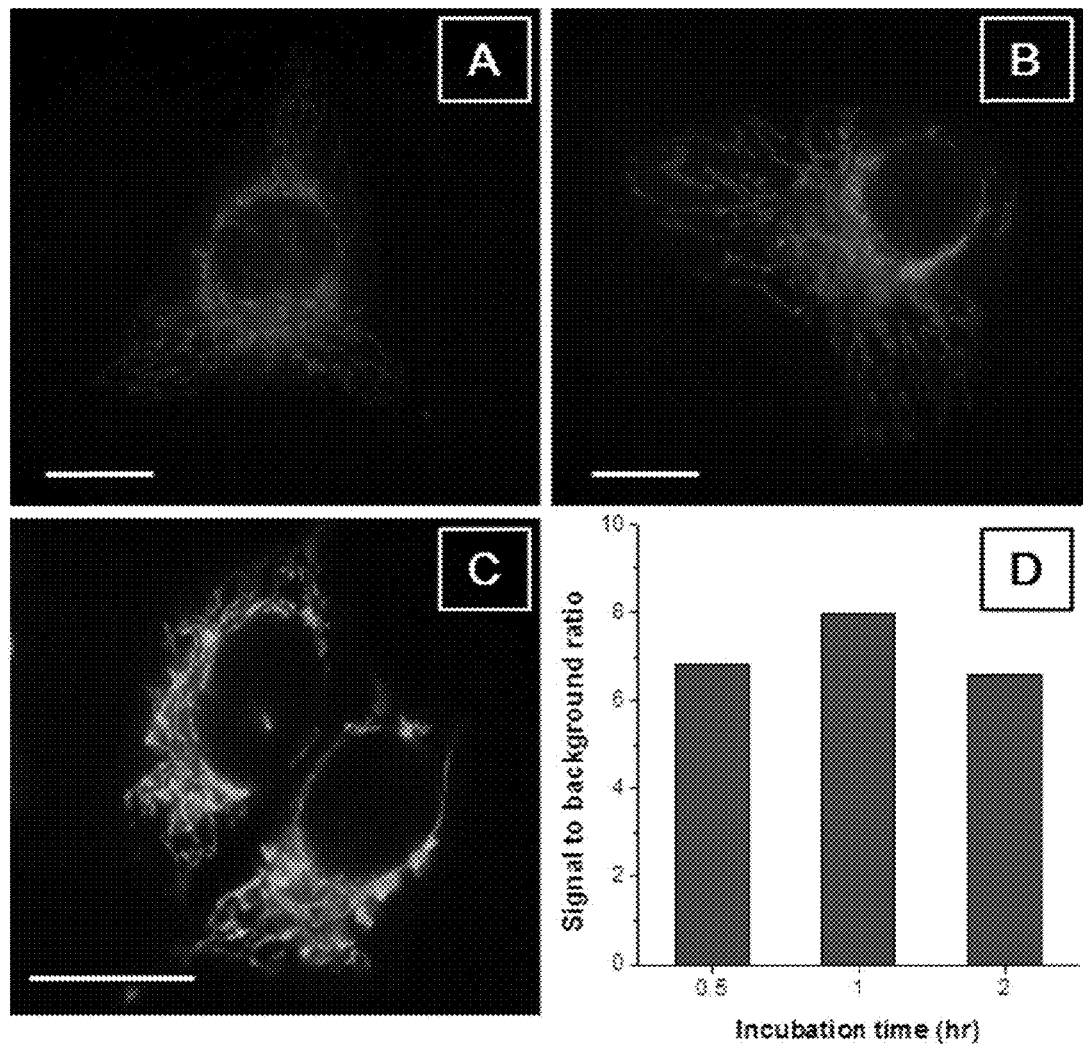
FIGS. 8A-8C show fluorescence images of the HeLa cells stained with TPE-TPP for (A) 30 min, (B) 1 h, and (C) 2 h.
FIG. 8D shows the signal to background ratio of TPE-TPP dyed HeLa cell with different incubation times. Concentration of TPE-TPP: 5 μM; excitation wavelength: 330-385 nm; scale bar: 15 μm.

A co-staining experiment with MitoTracker® Red FM (MT), a commercially available mitochondria imaging agent, suggested that the observed fluorescence from TPE-TPP is localized to the mitochondria of the living HeLa cells (FIG. 7). Pearson's correlation coefficient ($R_r$; from +1 to −1), which indicates the degree of linear dependence between two variables, is used to quantify the overlapping of the staining region between TPE-TPP and MT. Fluorescence signals of two dyes collected from two different channels are perfectly overlapped with $R_r$ to be 0.96, demonstrating the specific targeting of TPE-TPP on mitochondria.

Figure 9:
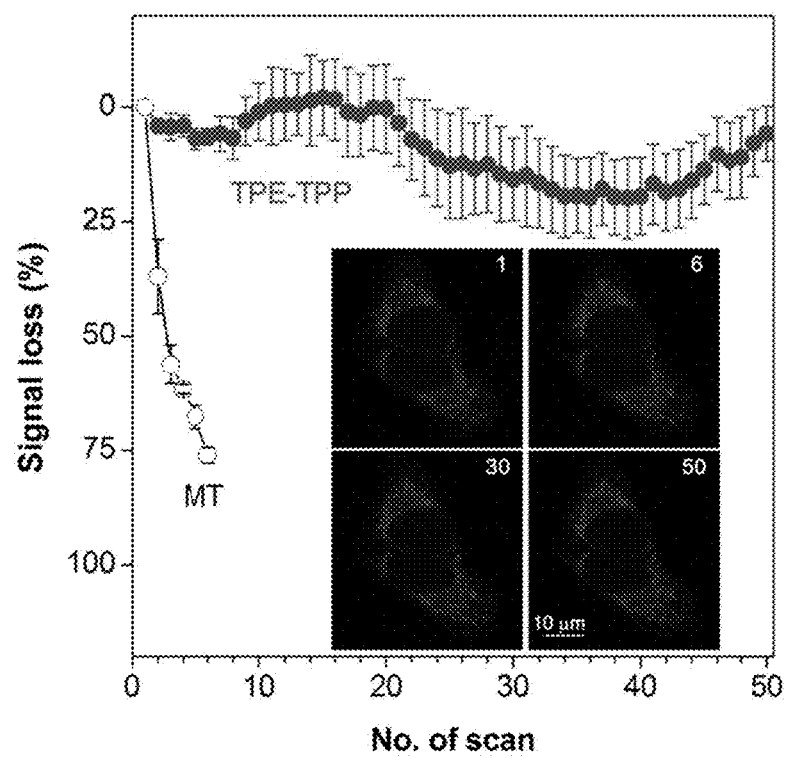
FIG. 9 shows signal loss (%) of fluorescent emission of TPE-TPP (solid circle) and MT (open circle) with increasing number of scans. Inset: example of fluorescent images of living HeLa cells stained with TPE-TPP (5 μM) with increasing number of scans (1-50 scans; the number of scan shown in the upper right corner of the panel). Excitation wavelength: 405 nm; emission filter: 449-520 nm; irradiation time: 7.75 sec/scan.

In FIG. 7A, cells were incubated with TPE-TPP for 1 h. However, staining time as short as 15 min is sufficient for TPE-TPP to enter and light up mitochondria in cells (data not shown). Incubation time between 30 min to 2 h gives similar high signal-to-noise ratio (FIG. 9).

The working concentrations of TPE-TPP and MT herein were 5 µM and 50 nM, respectively. At first glance, MT may appear more sensitive than TPE-TPP. However, it is actually disadvantageous for MT because, at such low concentration, the dye molecules can be easily photobleached by the strong excitation light especially in confocal microscopes. At higher concentrations, these probes tend to lose the specificity and stain other cellular structures.

Example 5

Figure 10:
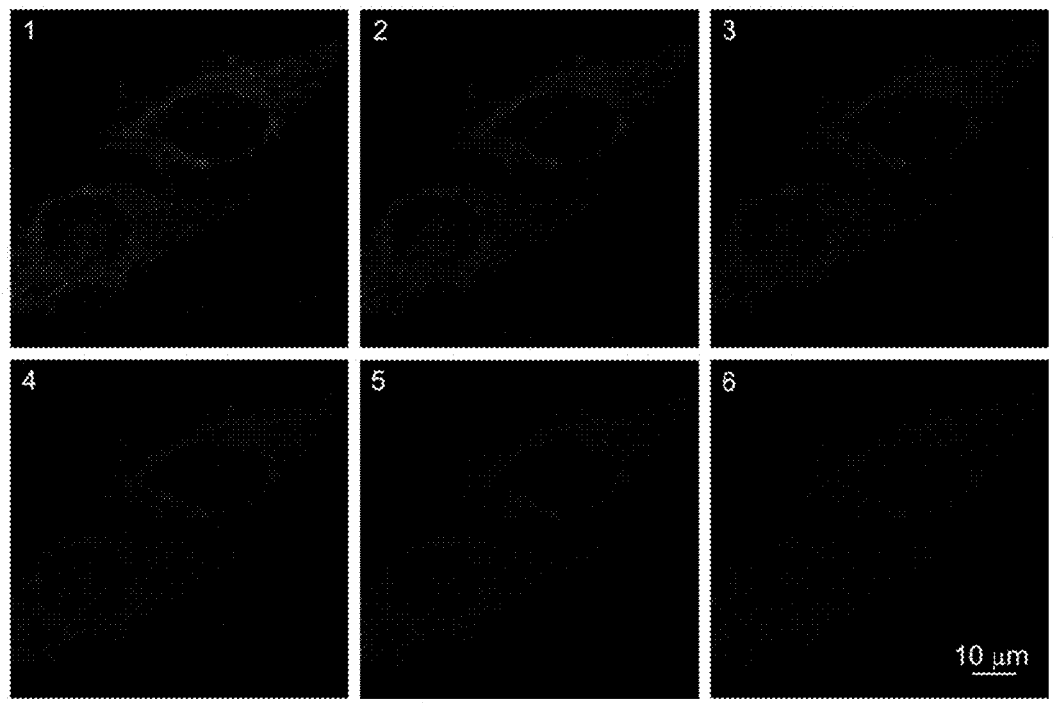
FIG. 10 shows fluorescent images of living HeLa cells stained with MitoTracker® Red FM with increasing number of scans (1-6 times). Concentration of MitoTracker® Red FM: 50 nM; excitation wavelength=560 nm; emission filter: 581-688 nm; irradiation time: 7.75 sec/scan.

Photostability is one of the most important criteria for developing fluorescent imaging agents. Continuous scanning by confocal microscope (Zeiss Laser Scanning Confocal Microscope LSM7 DUO) was used to quantitatively investigate the photostability of TPE-TPP and MT. Two dishes of HeLa cells subcultured from the same source were stained with 5 µM TPE-TPP for 1 h and 50 nM MT for 30 min, respectively. With the help of power meter, excitation power from 405 and 560 nm channels of the microscope were unified (65 µW) and used to irradiate the TPE-TPP and MT stained cells. The initial intensity referred to the first scan of TPE-TPP and MT stained cells was normalized and the percentage of fluorescence signal loss was calculated. As shown in FIG. 9, during 50 scans with total irradiation time of ~7 min, the signal loss of TPE-TPP is less than 20% and no significant difference was observed between the 1st and the 50th scan. Since live cells are dynamic, the movements of cells may attribute to the slight fluctuation of the signals. In contrast, the fluorescence signals of MT almost disappear after only 6 scans with less than 25% signal intensity remaining (FIG. 10).

Example 6

Figure 11:
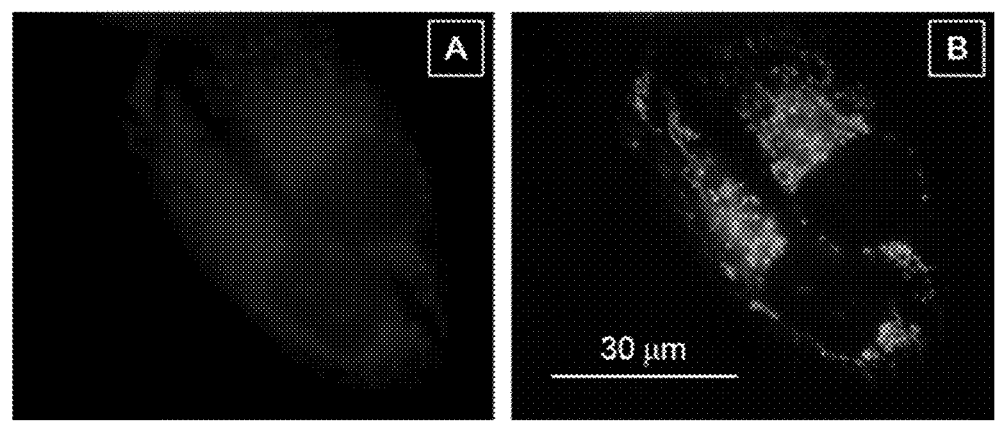
FIG. 11 shows fluorescent images of carbonyl cyanide m-cholorophenylhydrazone (CCCP; 10 μM) treated HeLa cells stained with (A) MT (50 nM) for 15 min and (B) TPE-TPP (5 μM) for 30 min. Excitation wavelength: 540-580 nm (for MT) and 330-385 nm (for TPE-TPP).

To test the tolerance of TPE-TPP and MT to the change of mitochondrial $\Delta\Psi_m$, carbonyl cyanide m-chlorophenylhydrazone (CCCP) was used to treat the cells prior to the staining procedure. CCCP is an uncoupler that causes rapid acidification of the mitochondria and dysfunction of ATP synthase resulting in the decrease of the mitochondrial $\Delta\Psi_m$. Upon treatment with 20 µM CCCP, the pH of mitochondria decreased about 0.7 and $\Delta\Psi_m$ thus decreased around 40 mV according to the Nernst equation. When the cells were treated with 10 µM CCCP, MT had no more specificity to mitochondria and the sensitivity became worse (FIG. 11A). Since the targeting of MT to mitochondria is driven by the huge $\Delta\Psi_m$, the decrease of $\Delta\Psi_m$ will affect the direction and accumulation of cationic MT to mitochondria. It was expected that similar phenomena would be observed for TPE-TPP as it shares a similar working principle. Surprisingly, under the same conditions, the specificity and sensitivity of TPE-TPP to mitochondria were perfectly retained in CCCP-treated cells (FIG. 11B).

Compared with MT, TPE-TPP carries two positive charges, which allows a wider dynamic range for mitochondrial targeting upon the change of $\Delta\Psi_m$. The lipophilicity may also play an important role in retaining the specificity and sensitivity of TPE-TPP in CCCP-treated HeLa cells. The lipophilicity of TPE-TPP is greatly enhanced by the TPE core with four phenyl rings rationalizing this phenomenon. On the other hand, MT carries only one positive charge and its selectivity is too susceptible to subtle change of $\Delta\Psi_m$ in mitochondria.

Figure 12:
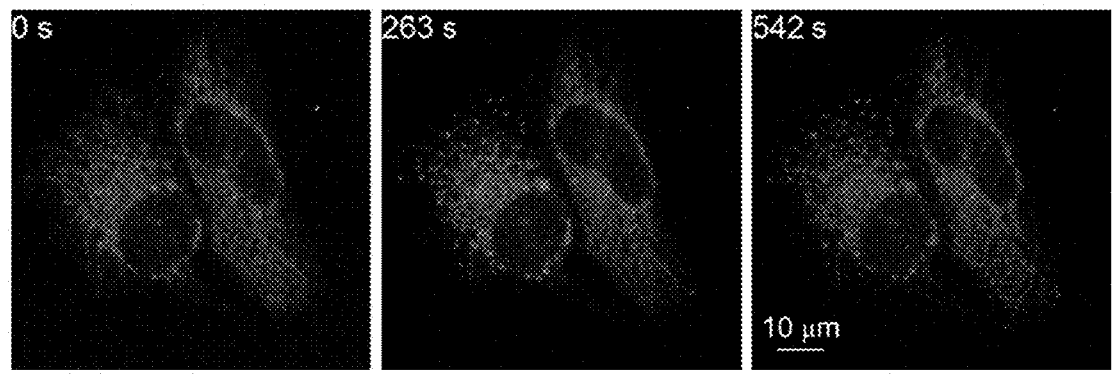
FIG. 12 shows an example of fluorescent images of CCCP (20 μM) treated living HeLa cells stained with TPE-TPP (5 μM) with increasing scan time (the scan time shown in the upper left corner of the panel). Excitation wavelength: 405 nm; emission filter: 449-520 nm; irradiation time: 15.49 sec/scan.

The high tolerance of TPE-TPP to the decrease of $\Delta\Psi_m$ enables the observation of change of mitochondrial morphology induced by CCCP. Upon exposure to CCCP, the reticulum-like mitochondria are gradually transformed to small and dispersed fragments (FIG. 12). The early stage of apoptosis involves remodeling of mitochondrial cristae and the consequent occurrence of morphological change of mitochondria, which is considered as an irreversible process associated with the collapse of $\Delta\Psi_m$. TPE-TPP has excellent specificity to mitochondria with outstanding photostability and tolerance to microenvironment change, representing a potential candidate of tracking agent for apoptosis studies.

Example 7

Figure 13:
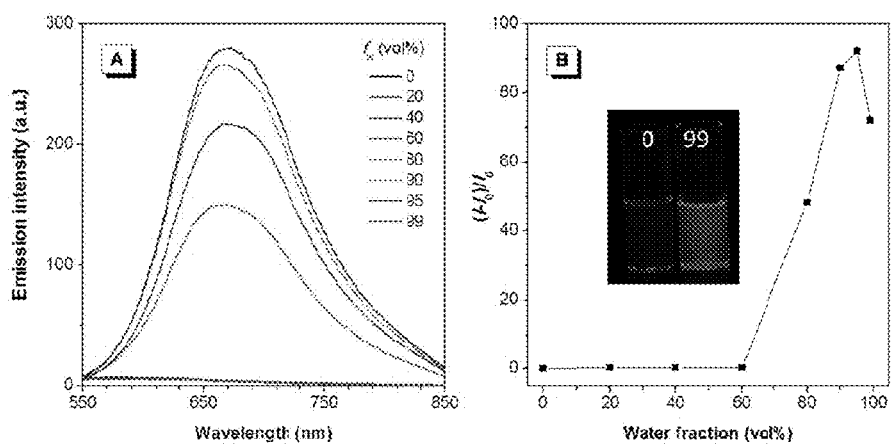
FIG. 13A shows emission spectra of TPE-MitoR in DMSO/water mixtures with different water fractions ($f_w$).
FIG. 13B shows a plot of relative emission intensity ($I-I_0/I_0$) versus the composition of the aqueous mixture of TPE-MitoR. $I_0$=emission intensity in pure DMSO solution. Inset in 13B: Photographs of TPE-MitoR in DMSO/water mixtures with $f_w$ values of 0 and 99% taken under 365 nm UV irradiation. Solution concentration: 10 μM; excitation wavelength: 450 nm.
Figure 14:
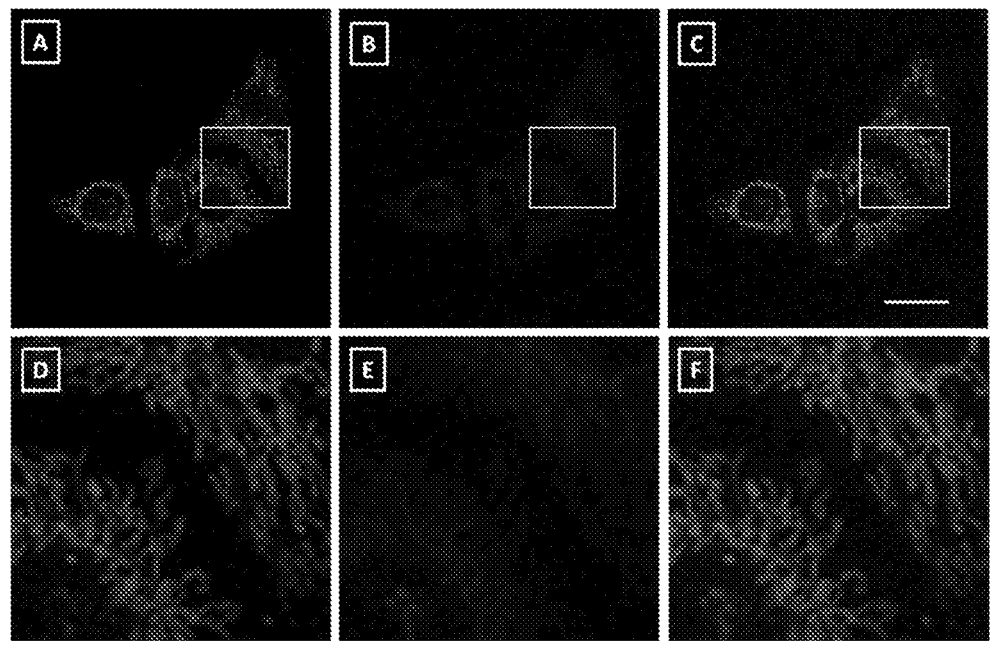
FIGS. 14A-14F show confocal images of HeLa cells stained with (A) TPE-MitoR (5 µM) for 30 min and (B) TPE-TPP (5 µM) for 30 min
Figure 15A:
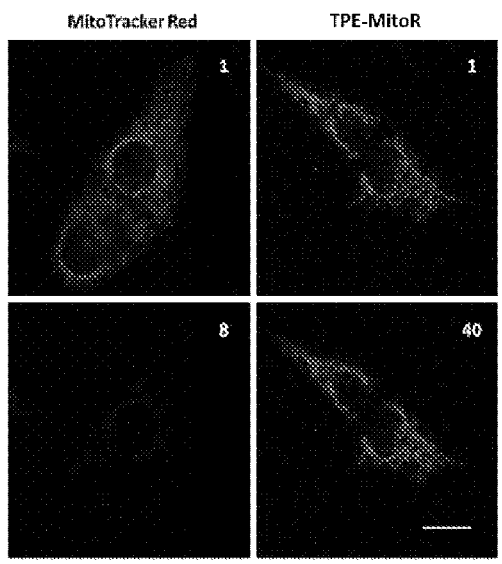
FIG. 15A shows confocal images of HeLa cells stained with MitoTracker Red and TPE-MitoR taken under continuous excitation at 560 nm and 488 nm for 9 and 40 scans, respectively. Scale bar: 20 µm.
Figure 15B:
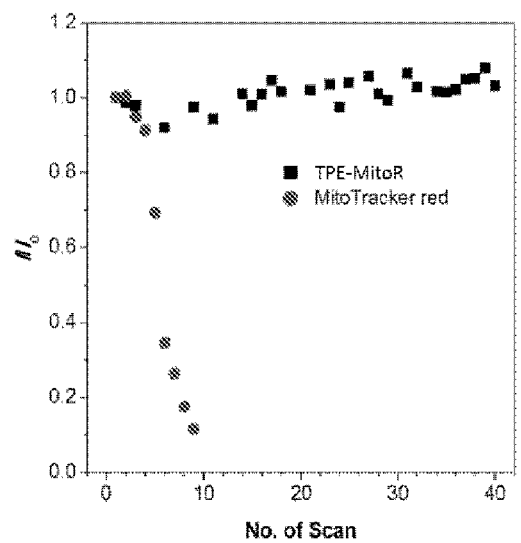
FIG. 15B shows luminescence decay curves of TPE-MitoR and MitoTracker Red with increasing number of scans.

An AIE luminogen targeting mitochondria specifically with red fluorescence emission was also synthesized, i.e., TPE-MitoR, (E)-1-ethyl-3,3-dimethyl-2-(2-(4'(1,2,2-triphenylvinyl)-[1,1'-biphenyl]-4-yl)vinyl)-3H-indol-1-ium hexafluorophosphate. TPE-MitoR showed typical AIE phenomenon while its fluorescence emission was greatly enhanced once poor solvent, DMSO, was added (FIG. 13). TPE-MitoR's ability for tracking mitochondria is evaluated by colocalizing with TPE-TPP (FIG. 14). TPE-MitoR showed promising result in locating mitochondria. Further, the photostability of TPE-MitoR is excellent while its fluorescence emission is kept steady even after forty scans (FIG. 15). However, the fluorescence emission of commercial mitochondria dye, MitoTracker Red, is completely quenched in less than ten scans.

Example 8

Figure 16:
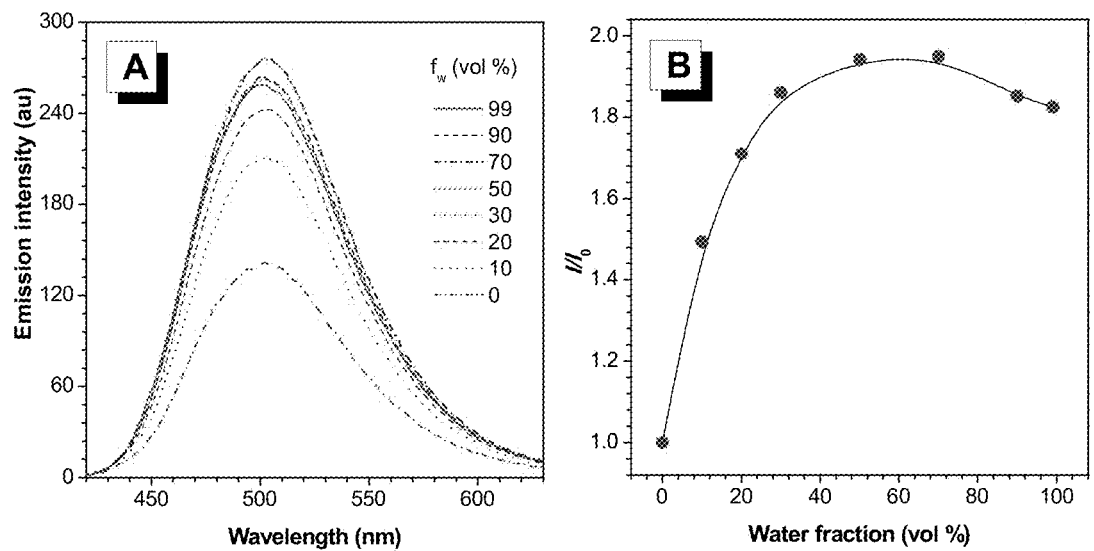
FIG. 16A shows emission spectra of TPE-IQ in DMSO/water mixtures.
FIG. 16B shows a plot of relative emission intensity ($I/I_0$) versus the composition of the aqueous mixture of TPE-IQ. Solution concentration: 10 µM; excitation wavelength: 390 nm.
Figure 17:
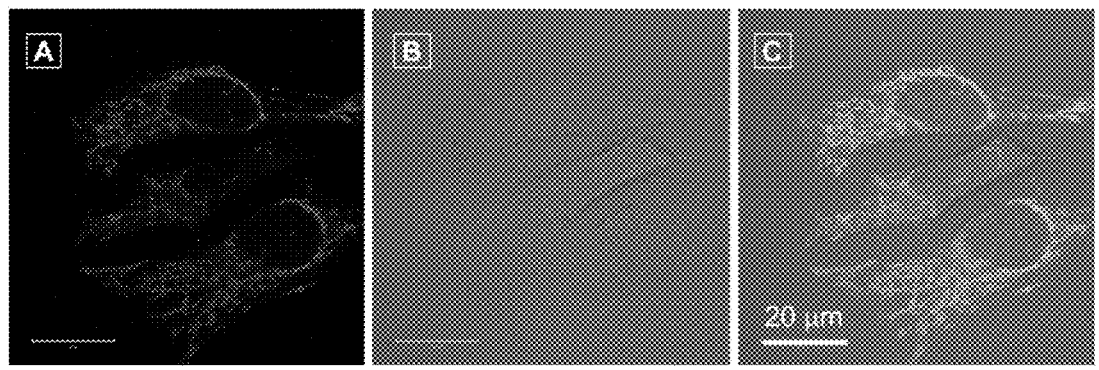
FIG. 17C shows panels A and B merged. Excitation wavelength: 488 nm (for TPE-MitoR) and 405 nm (for TPE-TPP). Scale bar: 20 µm.
FIG. 17A shows fluorescent and FIG. 17B shows bright field laser scanning confocal microscope images of HeLa cells stained with TPE-IQ (200 nM) for 10 min
Figure 18:
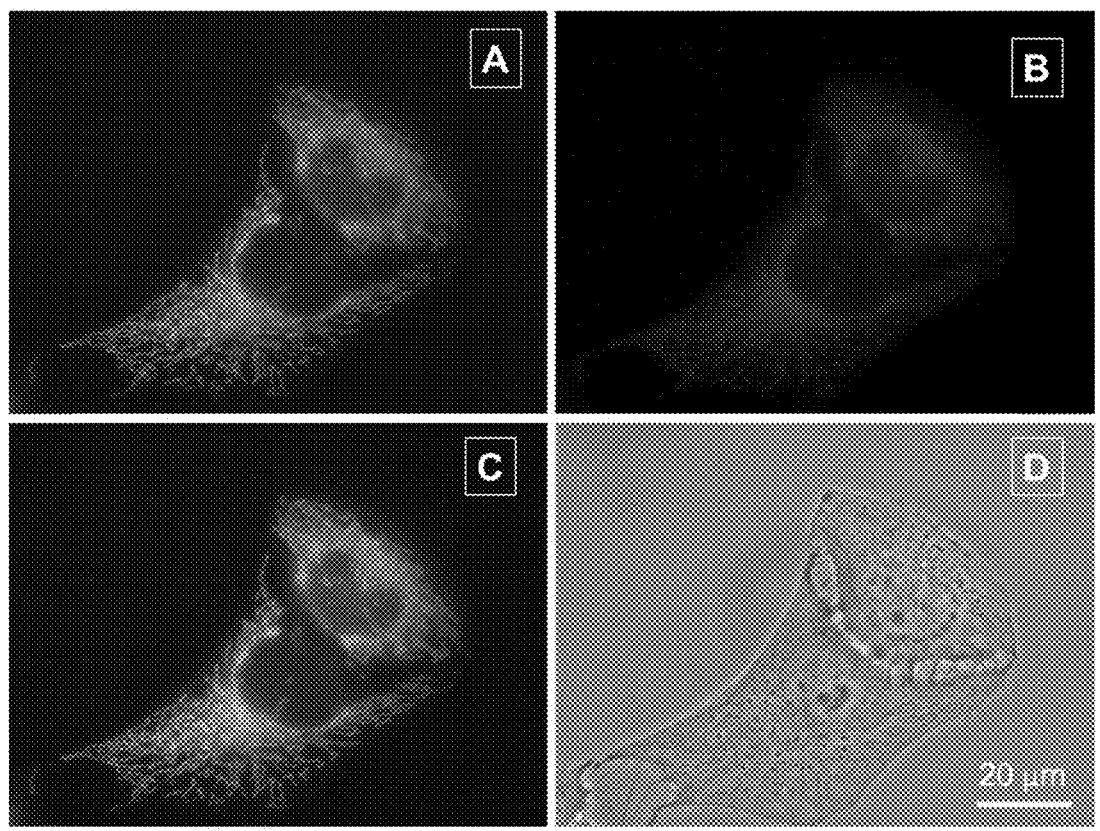
FIG. 18 shows fluorescent images of HeLa cells stained with (A) TPE-IQ (200 nM) for 15 min and (B) MitoTracker red FM (MT, 50 nM) for 15 min
Figure 19:
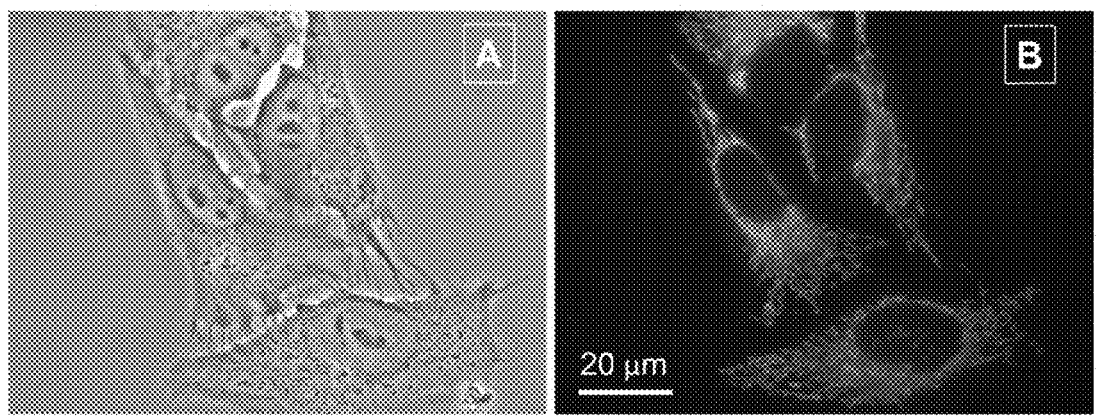
FIG. 19A shows bright field and FIG. 19B shows fluorescence images of Hela cell incubated with 500 nM of TPE-IQ for 1 min.

In another example, the AIE active TPE-IQ (3,4-diphenyl-2-propyl-6-(1,2,2-triphenylvinyl)isoquinolin-2-ium tetrafluoroborate) could also be utilized for mitochondria imaging. A DMSO solution of TPE-IQ emits faint light (FIG. 16). With the increase in water content, the emission of TPE-IQ can be further increased. TPE-IQ could enter the cell very fast even at relative low concentration, indicating its high affinity to the cell and mitochondria. In one experiment, 10 min incubation with 200 nM TPE-IQ was sufficient for lighting up the mitochondria (FIG. 17). Increases in dye concentration could further shorten the incubation time. When the cells were incubated with 500 nM of TPE-IQ for 1 min (FIG. 19), strong emission could be observed from the mitochondria of the cells. This could be developed into a washing-based mitochondria imaging probe.

Figure 20:
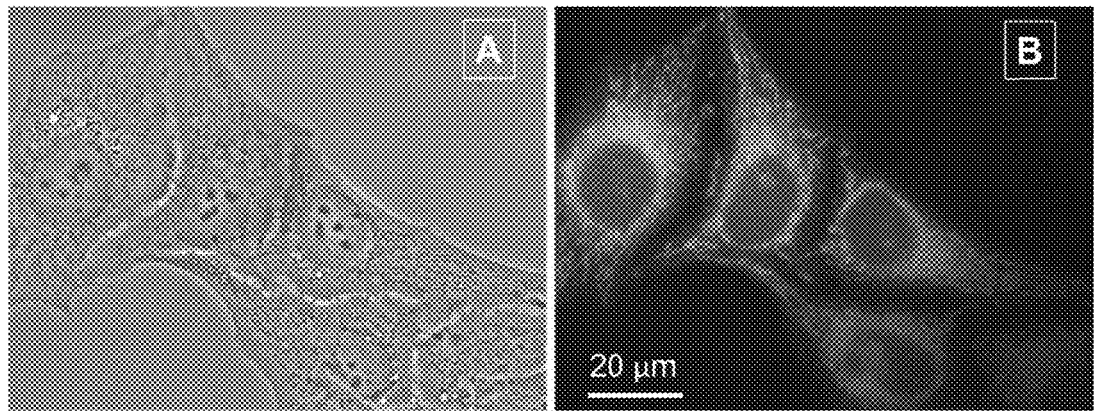
FIG. 20A shows bright field and FIG. 20B shows fluorescence images of Hela cell incubated with 500 nM of TPE-IQ for 10 min. The cells are pretreated with PFA for 50 min before incubation with TPE-IQ.

In addition, cell fixation is important for sample preserving. After 4% paraformaldehyde (PFA) fixation for 50 min, TPE-IQ could still target to the mitochondria of HeLa cells, suggestive of its potential application in fixed cell (FIG. 20). Taking into account the excellent stability and photostability of AIE materials, the TPE-IQ labelled cells may be preserved for a very long period of time.

Figure 21:
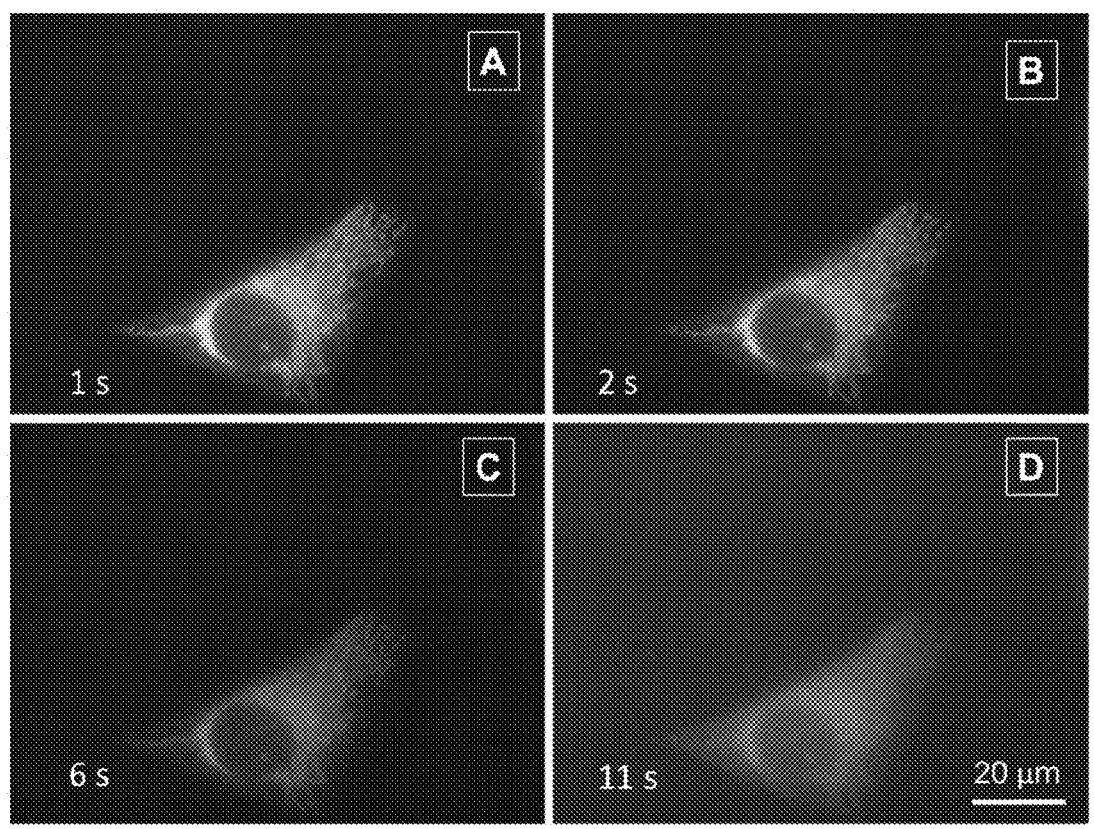
FIG. 21 shows fluorescent images of HeLa cells stained with TPE-IQ (1 µM) for 1 min after different UV irradiation time. (A) 1 s; (B) 2 s; (C) 6 s; (D) 11 s.
Figure 22:
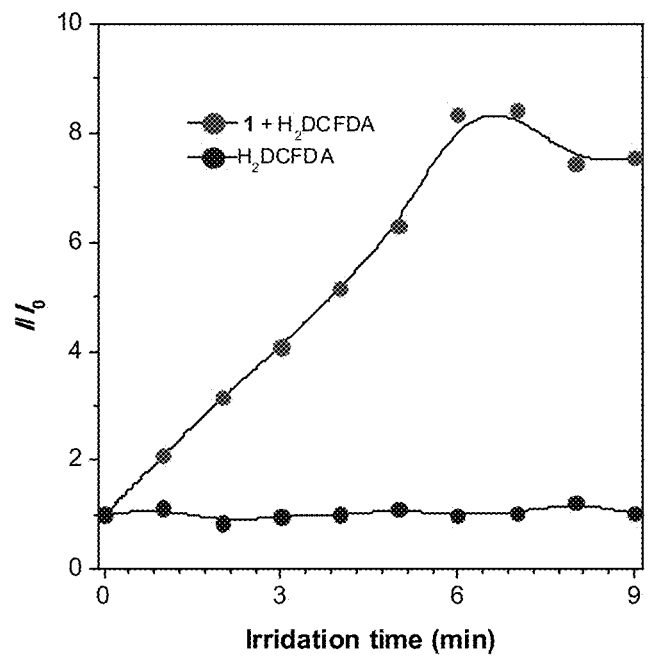
FIG. 22 shows change in fluorescence intensity at 521 nm after irradiation with UV light for different time. Concentration of TPE-IQ: 10 µM; concentration of $H_2DCFDA$: 1 µM.
Figure 23:
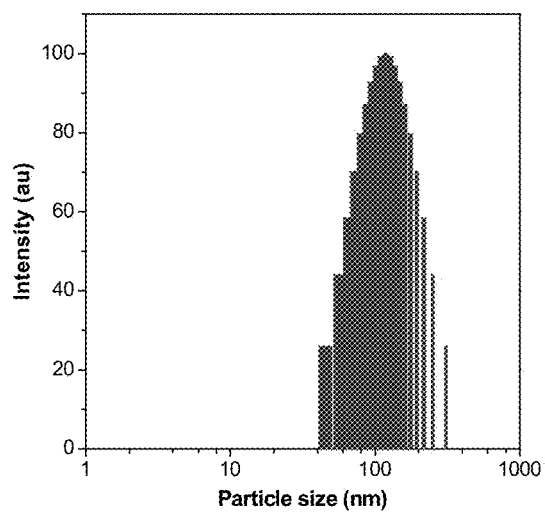
FIG. 23 shows particle size analysis of 200 nM TPE-IQ in MEM.

With UV irradiation, the morphology of mitochondria changed gradually, indicating the initiation of the cell apoptosis process. To prove that the apoptosis was initiated, the HeLa cell was irradiated with UV light for a relative short period of time (6 s) and then left in the dark for 15 min (FIG. 21). The morphology changed substantially. To understand the underlying mechanism of TPE-IQ induced cell apoptosis, reactive oxygen species (ROS) detection agent $H_2DCFDA$ was utilized. With continuous UV irradiation, the solution of TPE-IQ and $H_2DCFDA$ increased gradually, indicative of the production of ROS species (FIG. 22). This means that TPE-IQ could be utilized as a sensitizer for ROS generation, to induce cell apoptosis. Considering the mitochondria targeting of the probe, TPE-IQ could be used as an apoptosis inducer while enabling observation of the morphology change of the mitochondria at the same time. Besides, the probe may be utilized in phototherapy for selectively killing specific cells, while allowing for the study of how cells communicate when one cell undergoes the apoptosis process.

With the information contained herein, various departures from precise descriptions of the present subject matter will be readily apparent to those skilled in the art to which the present subject matter pertains, without departing from the spirit and the scope of the below claims. The present subject matter is not considered limited in scope to the procedures, properties, or components defined, since the preferred embodiments and other descriptions are intended only to be illustrative of particular aspects of the presently provided subject matter. Indeed, various modifications of the described modes for carrying out the present subject matter, which are obvious to those skilled in chemistry, biochemistry, or related fields are intended to be within the scope of the following claims.

We claim:

1. A luminogen having aggregation-induced emission properties comprising a triphenylphosphonium-functionalized, benzothiazolium-functionalized, or isoquinoline-functionalized TPE derivative, wherein the TPE derivative comprises a backbone structure of a formula:

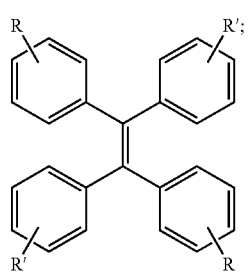

I or a salt thereof, wherein R and R' are each independently selected from the group consisting of

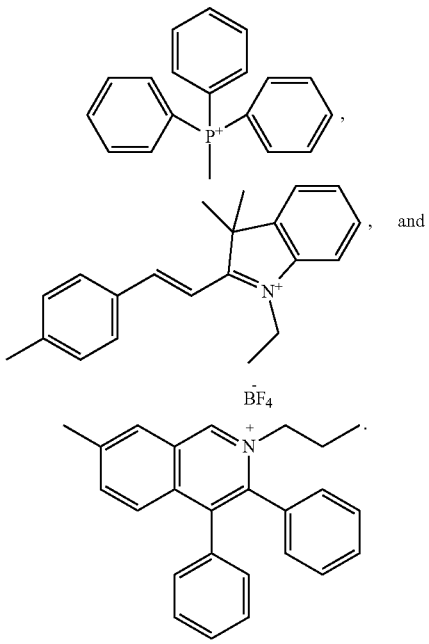

2. A method of imaging mitochondria in cells comprising:
contacting one or more live cells with a luminogen having aggregation-induced emission properties comprising a triphenylphosphonium-functionalized, benzothiazolium-functionalized, or isoquinoline-functionalized TPE derivative, wherein the TPE derivative comprises a backbone structure of a formula:

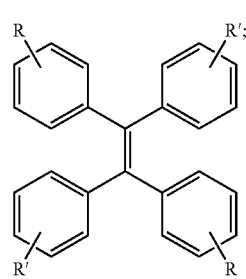

I or a salt thereof, wherein R and R' are each independently selected from the group consisting of

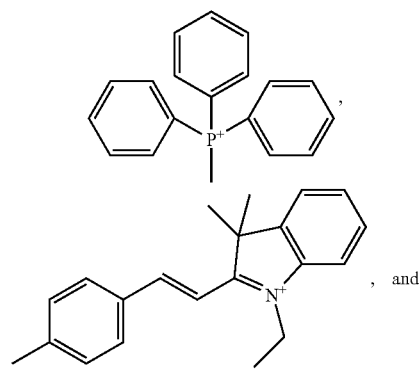

-continued

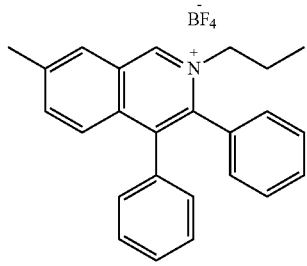

and imaging any mitochondrial activities.

3. The method of claim 2, wherein the TPE derivative enters mitochondria through electrophoretic force and lipophilic interaction, activating fluorescence of the TPE derivative.

4. The method of claim 2, wherein the living cells are living mammalian cells.

5. The method of claim 4, wherein the triphenylphosphonium-functionalized, benzothiazolium-functionalized, or isoquinoline-functionalized TPE Derivative is incubated with the living mammalian cells.

6. The method of claim 5, wherein fluorescence images are visualized by a fluorescence microscope and confocal microscope in the presence of the triphenylphosphonium-functionalized, benzothiazolium-functionalized, or isoquinoline-functionalized TPE Derivative with the living mammalian cells.

7. A method for in vivo monitoring of cell apoptosis comprising injecting a subject with the luminogen of claim 1 and detecting fluorescence, wherein the triphenylphosphonium-functionalized, benzothiazolium-functionalized, or isoquinoline-functionalized TPE Derivative is used as an apoptosis inducer.

* * * * *